(12) United States Patent
Lightner et al.

(10) Patent No.: US 7,563,942 B2
(45) Date of Patent: Jul. 21, 2009

(54) GENERATION OF PLANTS WITH ALTERED OIL CONTENT

(75) Inventors: Jonathan Lightner, Des Moines, IA (US); Hein Tsoeng Ng, Charlottesville, VA (US); John P. Davies, Portland, OR (US)

(73) Assignee: Agrinomics LLC, Portland, OR (US)

( * ) Notice: Subject to any disclaimer, the term of this patent is extended or adjusted under 35 U.S.C. 154(b) by 0 days.

(21) Appl. No.: 11/577,713

(22) PCT Filed: Oct. 20, 2005

(86) PCT No.: PCT/US2005/038132
§ 371 (c)(1),
(2), (4) Date: Apr. 20, 2007

(87) PCT Pub. No.: WO2006/047390
PCT Pub. Date: May 4, 2006

(65) Prior Publication Data
US 2007/0261130 A1    Nov. 8, 2007

Related U.S. Application Data

(60) Provisional application No. 60/621,226, filed on Oct. 22, 2004.

(51) Int. Cl.
C12N 15/82 (2006.01)
C12N 5/14 (2006.01)
C12N 5/04 (2006.01)
A21D 2/00 (2006.01)

(52) U.S. Cl. .................. 800/278; 435/468; 435/419; 426/622

(58) Field of Classification Search .................. None
See application file for complete search history.

(56) References Cited

U.S. PATENT DOCUMENTS

| | | | |
|---|---|---|---|
| 5,639,790 A | 6/1997 | Voelker et al. | |
| 5,704,160 A | 1/1998 | Bergquist et al. | |
| 6,229,033 B1 | 5/2001 | Knowlton | |
| 6,248,939 B1 | 6/2001 | Leto et al. | |
| 2006/0150283 A1* | 7/2006 | Alexandrov et al. | 800/288 |

FOREIGN PATENT DOCUMENTS

| | | |
|---|---|---|
| EP | 1 033 405 | 9/2000 |
| EP | 1033405 A2 * | 9/2000 |
| WO | WO01/083697 | 11/2001 |
| WO | WO03/002751 | 1/2003 |
| WO | WO03/020936 | 3/2003 |
| WO | WO 03/002751 * | 9/2003 |

OTHER PUBLICATIONS

Zou et al. (The Plant Cell, 9:909-923, 1997).*
Jako et al. (Plant Physiol. 126:861-874, 2001).*
Keskin et al. (Protein Science, 13:1043-1055, 2004).*
Thornton et al. (Nature structural Biology, structural genomics supplement, Nov. 2000).*
Guo et al. (PNAS, 101: 9205-9210, 2004).*
Wells, (Biochemistry 29:8509-8517, 1990).*
Ngo et al., (The Protein Folding Problem and Tertiary Structure Prediction, K. Merz., and S. Le Grand (eds.) pp. 492-495, 1994).*
Doerks et al., (TIG, 14:248-250, 1998).*
Smith et al. (Nature Biotechnology, 15:1222-1223, 1997).*
Bork et al. (TIG, 12:425-427, 1996).*
Broun et al. (Science, 282:1315-1317, 1998).*
Anoop et al., "Modulation of citrate metabolism alters aluminum tolerance in yeast and transgenic canola overexpressing a mitochondrial citrate synthase," *Plant Physiol.*, 132:2205-2217, 2003.
Beisson et al., "Arabidopsis genes involved in acyl lipid metabolism. A 2003 census of the candidates, a study of the distribution of expressed sequence tags in organs, and a web-based database," *Plant Physiol.*, 132:681-697, 2003.
Bert et al., "Comparative genetic analysis of quantitative traits in sunflower (*Helianthus annuus* L.). 2. Characterisation of QTL involved in developmental and agronomic traits," *Theor. Appl. Genet.*, 107:181-189, 2003.
Colbert et al., "High-throughput screening for induced point mutations," *Plant Physiol.*, 126(2):480-484, 2001.
Dehesh et al., "Overexpression of 3-ketoacyl-acyl-carrier protein synthase IIIs in plants reduces the rate of lipid synthesis," *Plant Physiol.*, 125:1103-1114, 2001.
Eastmond and Graham, "Re-examining the role of glyoxylate cycle in oilseeds," *Trends Plant Sci.*, 6(2):72-77, 2001.
Eccleston and Ohlrogge, "Expressions of lauroyl-acyl carrier protein thioesterase in *brassica napus* seeds induces pathways for both fatty acid oxidation and biosynthesis and implies a set point for triacylglycerol accumulation," *Plant Cell.* 10:613-621, 1998.
Fatland et al., "Molecular biology of cytosolic acetyl-CoA generation," *Biochem. Soc. Trans.*, 28(6):593-595, 2000.
Fatland et al., "Reverse genetic characterization of cytosolic acetyl-CoA generation by ATP-citrate lyase in *Arabidopsis*," *Plant Cell*, 17:182-203, 2005.
Feldmann et al., "A Dwarf Mutant of *Arabidopsis* Generated by T-DNA Insertion Mutagenesis," *Science*, 243(4896):1351-1354, 1989.
Focks and Benning, "wrinkled1: A novel, low-seed-oil mutant of *Arabidopsis* with a deficiency in the seed-specific regulation of carbohydrate metabolism," *Plant Physiol.*, 118:91-101, 1998.
Girke et al., "Microarray analysis of developing *Arabidopsis* seeds," *Plant Physiol.*, 124:1570-1581, 2000.
Jako et al., "Seed-specific over-expression of an *Arabidopsis* cDNA encoding a diacylglycerol acyltransferase enhances seed oil content and seed weight," *Plant Physiol.*, 126(2):861-874, 2001.
James and Dooner, "Isolation of EMS-induced mutants in *Arabidopsis* altered in seed fatty acid composition," *Theor. Appl. Genet.*, 80(2):241-245, 1990.

(Continued)

*Primary Examiner*—Phuong T Bui
*Assistant Examiner*—Vinod Kumar
(74) *Attorney, Agent, or Firm*—Klarquist Sparkman, LLP.

(57) ABSTRACT

The present invention is directed to plants that display an altered oil content phenotype due to altered expression of a HIO128.5 nucleic acid. The invention is further directed to methods of generating plants with an altered oil content phenotype.

9 Claims, No Drawings

OTHER PUBLICATIONS

Katavic et al., "Alteration of seed fatty acid composition by an ethyl methanesulfonate-induced mutation in *Arabidopsis thaliana* affecting diacylglycerol acyltransferase activity," *Plant Physiol.*, 108:399-409, 1995.

Katavic et al., "Utility of the *Arabidopsis FAE1* and yeast *SLC1-1* genes for improvements in erucic acid and oil content in rapeseed," *Biochem Soc. Trans.*, 28(6):935-937, 2000.

Larson et al., "Acyl CoA profiles of transgenic plants that accumulate medium-chain fatty acids indicate inefficient storage lipid synthesis in developing oilseeds," *Plant J.*, 32:519-527, 2002.

Lemieux et al., "Mutants of *Arabidopsis* with alterations in seed lipid fatty acid composition," *Theor. Appl. Genet.*, 80(2):234-240, 1990.

Lin et al., "The Pex16p homolog SSE1 and storage organelle formation in *Arabidopsis* seeds," *Science*. 284:328-330, 1999.

Lionneton et al., "Development of an AFLP-based linkage map and localization of QTLs for seed fatty acid content in condiment mustard (*Brassica juncea*)," *Genome*, 45(6):1203-1215, 2002.

Liu and Butow, "A transcriptional switch in the expression of yeast tricarboxylic acid cycle genes in response to a reduction or loss of respiratory function," *Mol. Cell. Biol.*, 19:6720-6728, 1999.

McCallum et al., "Targeted screening for induced mutations," *Nat. Biotechnol.*, 18(4):455-457, 2000.

Mekhedov et al., "Toward a functional catalog of the plant genome. A survey of genes for lipid biosynthesis," *Plant Physiol.*, 122:389-401, 2000.

Mitsuma et al., "Activation of phenylpropanoid metabolism in sesame by over-expression of carrot calmodulin gene," *Biol. Pharm. Bull.*, 27(10):1621-1625, 2004.

Moire et al., "Impact of unusual fatty acid synthesis on futile cycling through β-oxidation and on gene expression in transgenic plants," *Plant Physiol.*, 134:432-442, 2004.

Neuhaus and Emes, "Nonphotosynthetic Metabolism In Plastids," *Annu. Rev. Plant Physiol. Plant Mol. Biol.*, 51:111-140, 2000.

O'Hara et al., "Fatty acid and lipid biosynthetic genes are expressed at constant molar ratios but different absolute levels during embryogenesis," *Plant Physiol.*, 129:310-320, 2002.

Okuley et al., "*Arabidopsis* FAD2 Gene Encodes the Enzyme That Is Essential for Polyunsaturated Lipid Synthesis," *Plant Cell*, 6:147-158, 1994.

Pritchard et al., "Germination and storage reserve mobilization are regulated independently in *Arabidopsis*," *Plant J.*, 31(5): 639-647, 2002.

Rangasamy and Ratledge, "Compartmentation of ATP:Citrate lyase in plants," *Plant Physiol.*, 122:1225-1230, 2000.

Rangasamy and Ratledge, "Genetic enhancement of fatty acid synthesis by targeting rat liver ATP: citrate lyase into plastids of tobacco," *Plant Physiol.*, 122:1231-1238, 2000.

Ratledge et al, "Correlation of ATP/citrate lyase activity with lipid accumulation in developing seeds of *Brassica napus* L.," *Lipids*, 32(1):7-12, 1997.

Rawsthorne, S., "Carbon flux and fatty acid synthesis in plants," *Prog Lipid Res.*, 41:182-196, 2002.

Ruuska et al., "Contrapuntal networks of gene expression during *Arabidopsis* seed filling," *Plant Cell*, 14:1191-1206, 2002.

Rylott et al., "Co-ordinate regulation of genes involved in storage lipid mobilization in *Arabidopsis thaliana*," *Biochem Soc. Trans.*, 29:283-287, 2001.

Schnarrenberger and Martin, "Evolution of the enzymes of the citric acid cycle and the glyoxylate cycle of higher plants, A case study of endosymbiotic gene transfer," *Eur. J. Biochem.*, 269:868-883, 2002.

Schnurr et al., "Characterization of an acyl-CoA synthetase from *Arabidopsis thaliana*," *Biochem Soc. Trans.*, 28(6):957-958, 2000.

Shockey et al., "Characterization of the AMP-binding protein gene family in *Arabidopsis thaliana*: will the real acyl-CoA synthetases please stand up?" *Biochem Soc. Trans.*, 28(6):955-957, 2000.

Thelen et al., "Biotin carboxyl carrier protein isoforms in Brassicaceae oilseeds," *Biochem. Soc. Trans.*, 28(6):595-598, 2000.

Wada et al., "Role of a positive regulator of root hair development, Caprice, in *Arabidopsis* root epidermal cell differentiation," *Development*, 129(23):5409-5419, 2002.

White et al., "A new set of *Arabidopsis* expressed sequence tags from developing seeds. The Metabolic pathway from carbohydrates to seed oil," *Plant Physiol.*, 124:1582-1594, 2000.

Yadav et al., "Cloning of higher plant omega-3 fatty acid desaturases," *Plant Physiol.*, 103(2):467-476, 1993.

* cited by examiner

```
                         SEQUENCE LISTING

<160> NUMBER OF SEQ ID NOS: 11

<210> SEQ ID NO 1
<211> LENGTH: 450
<212> TYPE: DNA
<213> ORGANISM: Arabidopsis thaliana

<400> SEQUENCE: 1
atggcggatc aactcactga cgaacagatc tccgaattca aggaagcttt tagcctcttc        60
gacaaagatg gcgatggttg catcacaaca aaagagctgg aacagttat gcgttcacta       120 ggacaaaacc caacagaggc tgagctccaa gacatgatca acgaggttga tgcagatgga       180
aacggcacta tcgacttccc cgagttcctg aacctgatgg ctaagaagat gaaagacact       240
```

```
gactccgagg aagagctaaa agaagccttc agggttttcg acaaagacca gaacggtttc    300
atctccgctg ctgagctacg ccatgtgatg accaatcttg gtgagaagct aactgatgaa    360
gaagtggaag agatgatccg tgaggctgat gttgatggag atggtcagat taactatgaa    420
gagtttgtca agattatgat ggctaagtga                                     450

<210> SEQ ID NO 2
<211> LENGTH: 149
<212> TYPE: PRT
<213> ORGANISM: Arabidopsis thaliana

<400> SEQUENCE: 2

Met Ala Asp Gln Leu Thr Asp Glu Gln Ile Ser Glu Phe Lys Glu Ala
1               5                   10                  15

Phe Ser Leu Phe Asp Lys Asp Gly Asp Gly Cys Ile Thr Thr Lys Glu
                20                  25                  30

Leu Gly Thr Val Met Arg Ser Leu Gly Gln Asn Pro Thr Glu Ala Glu
            35                  40                  45

Leu Gln Asp Met Ile Asn Glu Val Asp Ala Asp Gly Asn Gly Thr Ile
        50                  55                  60

Asp Phe Pro Glu Phe Leu Asn Leu Met Ala Lys Lys Met Lys Asp Thr
65                  70                  75                  80

Asp Ser Glu Glu Glu Leu Lys Glu Ala Phe Arg Val Phe Asp Lys Asp
                85                  90                  95

Gln Asn Gly Phe Ile Ser Ala Ala Glu Leu Arg His Val Met Thr Asn
                100                 105                 110

Leu Gly Glu Lys Leu Thr Asp Glu Glu Val Glu Glu Met Ile Arg Glu
            115                 120                 125

Ala Asp Val Asp Gly Asp Gly Gln Ile Asn Tyr Glu Glu Phe Val Lys
        130                 135                 140

Ile Met Met Ala Lys
145

<210> SEQ ID NO 3
<211> LENGTH: 846
<212> TYPE: DNA
<213> ORGANISM: Artificial sequence
<220> FEATURE:
<223> OTHER INFORMATION: chimeric polynucleotide

<400> SEQUENCE: 3
cgagcgcccc gtttattccc ctccggcgca gccgcccccc gtgtcctgtg cgcaccttct     60
cgaagcctcc tccctccctc ccccatggcg gaccagctca ccgacgagca gatcgccgag    120
ttcaaggagg ccttcagcct cttcgacaag gatggcgacg gttgcatcac caccaaggag    180
ctcggaaccg tgatgcggtc ccttgggcag aaccccacgg aggcggagct gcaggacatg    240
atcaacgagg ttgacgcgga cggcaacggc accatcgact cccggagtt cctgaacctg    300 atggcgagga agatgaagga cactgactcg gaggaggagc tcaaggaggc gttccgcgtg    360
tttgacaagg accagaacgg cttcatctcg gcggcggagc tgcgccacgt gatgaccaac    420
ctcggggaga agctgacgga cgaggaggtg gacgagatga tccgggaggc ggacgtggac    480
ggcgacggcc agatcaacta cgaggagttc gtcaaggtca tgatggccaa gtgaggtggc    540
gaggacaggg ggtgtcctcc cacgaaataa gcttaaaatt tgctctcaag tggattggaa    600
tggaatgcca gacagactcg caaggttgta ttttgtgcta tgcgcctgtt ttttttaagta    660
```

-continued

```
ctgttgcctg ttgggtagtt ggtcgggtta tcttgtagcg gtgtagtcgt ggggagcagc    720
atcggaatta cctggtttct agtcttatca tggaatttag gggctttgtg caaatctcgg    780
ttttgccctg cggtttgctt gtatgcttgc tccaaaatgc tggccggaag tacattttgt    840
ggattc                                                                846
```

<210> SEQ ID NO 4
<211> LENGTH: 828
<212> TYPE: DNA
<213> ORGANISM: Artificial sequence
<220> FEATURE:
<223> OTHER INFORMATION: chimeric polynucleotide
<220> FEATURE:
<221> NAME/KEY: misc_feature
<222> LOCATION: (781)..(781)
<223> OTHER INFORMATION: n is a, c, g, or t
<220> FEATURE:
<221> NAME/KEY: misc_feature
<222> LOCATION: (786)..(787)
<223> OTHER INFORMATION: n is a, c, g, or t

<400> SEQUENCE: 4

```
cgcacgctct catcattttc cttctgctac cttctctcaa cccaaacaca tatttcccag     60 gaaaagaaa  aagcttgagc gaacaagaaa atggccgatc agcttaccga cgatcagatc    120
tctgaattca aggaggcctt tagcctgttc gacaaggatg agatggttg  cattactacc    180 aaggagttgg gaactgtgat gcgatcactt gggcagaacc ccactgaggc agaactgcaa    240
gatatgatta tgaagtcga  tgctgatgga atgggacca  ttgattttcc tgaattcctt    300
aacctgatgg caagaaaaat gaaggataca gactctgagg aggagcttaa agaggcattc    360
agggtgtttg acaaggatca gaatgggttc atttctgcag ccgagctgcg ccatgtcatg    420
acaaaccttg gtgaaaagct tacagatgag gaagtcgacg agatgatccg ccgaagccga    480
tgtttgatgg tgatgggcag atcaactacg aggagttcgt caaagtcatg atggccaagt    540
aaaggacctc tccaactata accaggatta aaaaatgggg tttaaaaaaa aaggaagaaa    600
ggaacagggc agataagttt gctaaaatat ctattaatga ataggacatc aatgtttta     660 agttacaagc ttttgttgga tggtttcttt gttcatgttt gcattttttt gtggaccgaa    720
ccttagtatt atgcttgttt gctctgcttt tttgttcagt agtgctgggt tgttaacgtc    780
nataannaaa aaaaaaaaa  aaaaaaaaa  aaaaaaaaa  aaaaaaat               828
```

<210> SEQ ID NO 5
<211> LENGTH: 764
<212> TYPE: DNA
<213> ORGANISM: Artificial sequence
<220> FEATURE:
<223> OTHER INFORMATION: chimeric polynucleotide

<400> SEQUENCE: 5

```
aacaccccat gcaatgcaac gtacacgaga tacaagactc gcacaaaaga tccaaaaccc     60
cctgaaaata tgagcttaca acaaatccta aaagctccag caggagcaat aatgcaagat    120
aacatcacaa tcaaaagaga ccaggtatct gatgtcgagt tcccatgact acaccaccta    180
aaccgaccac tactagacat tacctcctgc atgatactga tgtgtactca aaagggacat    240
ggcaaagtac agcttgtgtg cctgatattt cacttcaatt cattcataga taacgggat     300 cgctcctcac ttggccatca tgaccttgac gaactcctcg tagttgatct ggccgtcgcc    360
gtcaacatcg gctcacggga tcatctcgtc gacctcctcg tcagtcagct tctcgccgag    420
gttggtcatg acatggcgga gctcagcagc cgagatgaaa ccattctggt ccttgtcgaa    480
```

```
gacgcgaaag gcctccttaa gctcctcctc ggagtcggtg tccttcatct tccttgccat    540
caggttcagg aactctggga agtcaatggt cccattgcca tcagcatcaa cctcgttgat    600
catgtcctgc agctctgctt cagtggggtt ctggccaagg gagcgcatca cagttccaag    660
ctccttggta gtgatgcagc cgtcgccatc cttatcgaag aggctgaagg cctccttgaa    720
ctccgcgatc tgctcgtccg tgagctggtc cgccatggaa gatg                     764
```

<210> SEQ ID NO 6
<211> LENGTH: 1009
<212> TYPE: DNA
<213> ORGANISM: Artificial sequence
<220> FEATURE:
<223> OTHER INFORMATION: chimeric polynucleotide

<400> SEQUENCE: 6

```
ggggcacgag gcacactctc tctcaccaaa gccttcctag aacgaaaaaa aaaagaagag     60 caatttccc tcaccaaaga agaagaagca aacaatggcc gatcaactta ccgatgaaca    120
gatctccgag ttcaaggaag ccttcagctt gttcgacaag gacggcgatg gttgcatcac    180
aaccaaggag cttggaactg ttatgcgttc attggggcaa acccaactg aggcagagct    240 ccaggacatg atcaatgaag tggatgctga tgggaatggt accattgact tccctgagtt    300
cctaaatctc atggccagga gatgaaggga cactgattct gaggaggagc tgaaagaggc    360
attccgggtt ttcgacaagg accagaatgg gttcatctct gctgctgagc tccgccatgt    420
gatgaccaac ctcggggaga agctcaccga tgaagaggtt gatgagatga ttcgcgaggc    480
cgatgttgat ggcgatggcc aaataaacta cgaggagttc gttaaggtga tgatggccaa    540
gtgatcatca cattatggcc acaaaaacct aaatgaagaa atgttgatta aaggaaacg    600 acaaaaaaag gggtaggagg aaggccaagg gtttgggtgg tataacagtg atgtagtagt    660
ccttgacctt tcttcttcct acatttttat ttgatggttt ttgaatccaa ccttaaaatg    720
tcaattagtg gcaagtcctg ctactaggct gtagtggaac tgaaccttct tagtttgtct    780 tgtaattta tccaaaaaaa gggttgtaat gttaatgtct cttcactttc tgccactcct    840 catttttta aagatgatga atattgtgat gatatttgac atgcatctta gtttacttga    900
aaagccattg tgtgatatgg attctcctaa aaaaaaaaa aaaaaaaaaa aaaaaaaaa    960 aaaaaaaaa aaaaaaaaa aaaaaaaaa aaaaaaaaa aaaaaaaa                    1009
```

<210> SEQ ID NO 7
<211> LENGTH: 856
<212> TYPE: DNA
<213> ORGANISM: Artificial sequence
<220> FEATURE:
<223> OTHER INFORMATION: chimeric polynucleotide

<400> SEQUENCE: 7

```
ggacgcgctc ttttctctct ctctcagatt tttttaattt ccgtctagac ttttgccttt     60
cagtttgtta agaacagtc gttaaagaga aatggcggat caattgactg atgaccagat    120
ctccgagttc aaggaagctt tcagtttgtt cgataaggat ggtgatggtt gcatcaccac    180
caaggaattg gggactgtca tgagatcgct aggacagaac ccaacagagg cagaactcca    240
ggacatgatt aacgaggttg atgctgatgg aaatggtacc attgattttc ctgagttcct    300
gaacctcatg gcaaggaaga tgaaggatac cgactctgag gaggagctca agaggcatt    360 cagagttttt gacaaggatc agaatggttt catctctgcg gccgagctcc gtcatgtgat    420
```

-continued

```
gactaatctc ggtgagaagc ttactgatga agaggtcgat gagatgatca gagaagctga    480
tgtggatggc gatggccaga taaattatga ggaatttgtc aaggttatga tggctaagtg    540
atatccctcc cccccgggaa aaatatttt tataaattta aattaggagg ggataatagg     600
gttgacctat ataatgaaat ttctatattt tatggttttt tgaatcgagg cgcttaaggg    660
aagtggtgtt ggtggcttat tgtggtggtt ttgttgtaac gttcacgctt cctttaatgt    720
cttgtgaaac tcggttgcct ttgccagttt atattttgct tatttgatct tttgtaaact    780
tgaactactt gggaagatcg agcctgagcc tgtatgttga atggatgacc aattctatat    840
ttggtcactt tctgct                                                    856
```

<210> SEQ ID NO 8
<211> LENGTH: 854
<212> TYPE: DNA
<213> ORGANISM: Artificial sequence
<220> FEATURE:
<223> OTHER INFORMATION: chimeric polynucleotide

<400> SEQUENCE: 8

```
gccactcgtt cccctttcctt cctctcctcc tctcgcggaa ccttctcgaa gcttccacac    60
ccccaacctc gcctccacca ccaacccccc atggcggacc agctcaccga cgagcagatc    120
gccgagttca aggaggcgtt cagcctcttc gacaaggacg cgacggttg catcactact      180 aaggagcttg aaccgtgat gcggtccctt ggtcagaacc caactgaggc ggagctgcag      240
gacatgatca cgaggttga tgctgatggc aatgggacca ttgacttccc agagttcctg      300
aacctgatgg cgaagaagat gaaggatacc gactctgagg aggagctcaa ggaggccttc    360
cgtgtgtttg acaaggacca gaacggtttc atctcggctg ctgagctccg ccacgtcatg    420
accaaccttg gtgagaagct gaccgacgag gaagtcgacg agatgatccg tgaggctgac    480
gtcgatggcg atggccagat caactacgag gagttcgtta aggtcatgat ggccaagtga    540
ggagggttcc cattaaataa gttctgtctg aagtgaacta aaactgtcag gcctacaac      600 aaagctgtac tttgtgatgt tccttttaag tacctatctt tgctggtggt aatgttgagt    660
agcgatcggg ttaggtggtc tagtcatgag aaacaacatc agatgcctgg tttcttttga    720
ttgtgatgct tatcttgcgc ctgccggagc ataggatttg ttggggtttc atcatttttc    780
ttggatcgtt gtgcagatat gcattgcctg gttccttct atcatcatct ttacttcaaa     840
aaaaaaaaaa aaaa                                                      854
```

<210> SEQ ID NO 9
<211> LENGTH: 1116
<212> TYPE: DNA
<213> ORGANISM: Artificial sequence
<220> FEATURE:
<223> OTHER INFORMATION: chimeric polynucleotide

<400> SEQUENCE: 9

```
aagctctgtg aattaatcga taatggcgga tcagctcact gacgatcaga tctcggagtt    60
caaagaagct tttagcctat tcgacaagga tggagatggt tgcatcacaa ctaaggagct    120
tggaaccgtg atgcggtcat tggggcagaa cccaactgag gctgagcttc aagacatgat    180
caatgaagtt gatgctgatg gaatgggac cattgacttc cctgagttcc ttaacctgat     240
ggctcgcaag atgaaggaca ctgattctga ggaggagctc aaggaagctt tagagtgtt     300 tgacaaggat cagaatggat ttatctctgc tgctgagctt cgccatgtca tgactaacct    360
aggtgagaag cttacagatg aagaggttga tgagatgatt cgtgaagctg atgtggatgg    420
```

```
tgatggacag atcaactatg acgagtttgt caaggtcatg atggccaaaa attttgagtt      480
ctgatggact tgtgtcgttg gtcacaagtt cgactcttgt gtcaagcaat ccaagtctaa      540
tgcataagtg aagaatgata ggtggttgaa cccattgttc ctcagtctcg aaagctaatg      600
gtttcatgaa gtgaaaggtc gcgaaatgaa gttcaaaatt gtctaccaaa ggcgctagcg      660
tgtaccctgg ggtgttcatc atcactcata tctcatctca agacaatgga acctgtaacc      720
cgcctgcttc tagctttcgt tctcttttga cgatatcata aaactttta catgccttct       780 actaatataa cttctatttt ccctttatc ttcttttcag tgtcttcctc tatttaaatg       840
ccattttcga ggtgtataga atctagttcc gaggaaggga atcgttggag caatgattta      900
gttatcttct tagggtatat aggttattgg ttcagtcgt gaaatcaacc ttcaacggct       960
gcatcaggta ggttacatat atcacatttc ttaggttgtg gcctttcttt gaatcacgtt     1020
tgcgcgaagt ccttgatgtt tgtttcaacc aggttgtttg gagggttct tccttgagtg      1080 agattttttg tgcatcgagc tatcattttc acttga                                1116

<210> SEQ ID NO 10
<211> LENGTH: 862
<212> TYPE: DNA
<213> ORGANISM: Artificial sequence
<220> FEATURE:
<223> OTHER INFORMATION: chimeric polynucleotide

<400> SEQUENCE: 10
gctttaatta tatttaccat gaaatctgta gttttggta taaaagcagc aatcttctca        60
taattccaaa atccatacag agctgaaaat ttttcaaaaa atttgtgtga aattctagaa      120
tcatcttctc tgtgattact agaagaagaa aaatggcgga tcagcttact gatgaccaga      180
tctctgagtt caaagaggct ttcagcttgt tcgacaagga cggagatggt tgcatcacga      240
ctaaggagct tgggactgtg atgaggtcgt tgggacagaa ccctactgaa gctgaactcc      300
aggacatgat aaacgaggtg gatgcagatg gtaatggaac catcgacttc ccagagtttc      360
taaacctcat ggccaggaag atgaaggata ctgactctga ggaggagttg aaagaggcat      420
tcagagtttt cgacaaggat caaaatggct tcatctcagc tgctgagctt cgtcatgtga      480
tgactaacct tggagaaagc ttactgatga agaagtcgat gagatgatta gggaagcaga      540
tgttgatggt gatggacaaa tcaactatga ggagtttgtt aaggtcatga tggccaagta      600
attccaccat cctcttgtta catttgaagt ttagacttgt caaaaatgtg aaaaaaagcc       660
aaaaataatt cattggatgg gatcttgtct agtataatgt aagtcttacc atctcgatgt      720
attgaacctt cattgaatgt aatgttttat tgtaagggtg gtgtaatctc tacttatttt      780
cttgaagttt atgtactttc tttgatcctc ttagttgatg aatgcaattt tatgagggta      840
atttcctcat agtttagtat gc                                               862

<210> SEQ ID NO 11
<211> LENGTH: 878
<212> TYPE: DNA
<213> ORGANISM: Artificial sequence
<220> FEATURE:
<223> OTHER INFORMATION: chimeric polynucleotide

<400> SEQUENCE: 11
gcacgaggga aacctcgccc ctcattttca cccattttc ctctcctctc tcttcacgat        60
ctctctttct ctctcctcta aacaatggcc gatcaactca gcgacgatca gatctctgaa      120
```

-continued

```
tttaaggaag ccttcagcct atttgacaaa gatggagatg gctgtatcac caccaaggaa      180
cttggaacag tgatgcgttc gcttggacaa aacccaactg aagcagagct ccaggacatg      240
ataaatgaag tcgatgctga tggaaatgga acaatcgact tccccgaatt cctcaatctg      300
atggcgagga agatgaagga caccgactca gaggaggagc tgaaggaagc tttccgagtt      360
tttgacaagg atcaaaatgg ttttatttct gcagccgagc ttcgccacgt gatgacgaac      420
cttggtgaaa agctgacaga tgaagaagtt gacgagatga tccgtgaggc tgatgtggat      480
ggtgatggtc agatcaacta tgaggaattc gtcaaggtta tgatggccaa gtgagaatca      540
tcgagtctta actcaaaccc ttgaactaat acaggacagg gcagataagt tagatgagat      600
tttccaaatt ctatctcctc taggataaaa ctcatggcac tatttatagt tttttttttg      660
gtggtggttt gtttttcttg cttgcattga tggtgtaggt gaaatctttt gtgctatctg      720
cttgtctgcc cctgtcccga attctagaaa gtttcggggt tgatagtctt ttgtttttt       780 aagctctatt agagttttaa actttggata ttatgaactg agaacaattg gattaaatta      840
tatggtcttt tggggtgtct aaaaaaaaaa aaaaaaa                                878
```

GENERATION OF PLANTS WITH ALTERED OIL CONTENT

REFERENCE TO RELATED APPLICATIONS

This is the § 371 U.S. National Stage of International Application No. PCT/US2005/038132, filed Oct. 20, 2005, which was published in English under PCT Article 21(2), which in turn claims the benefit of U.S. Provisional Application No. 60/621,226, filed Oct. 22, 2004, the contents of both of which are hereby incorporated by reference.

BACKGROUND OF THE INVENTION

The ability to manipulate the composition of crop seeds, particularly the content and composition of seed oils, has important applications in the agricultural industries, relating both to processed food oils and to oils for animal feeding. Seeds of agricultural crops contain a variety of valuable constituents, including oil, protein and starch. Industrial processing can separate some or all of these constituents for individual sale in specific applications. For instance, nearly 60% of the U.S. soybean crop is crushed by the soy processing industry. Soy processing yields purified oil, which is sold at high value, while the remainder is sold principally for lower value livestock feed (U.S. Soybean Board, 2001 Soy Stats). Canola seed is crushed to produce oil and the co-product canola meal (Canola Council of Canada). Nearly 20% of the 1999/2000 U.S. corn crop was industrially refined, primarily for production of starch, ethanol and oil (Corn Refiners Association). Thus, it is often desirable to maximize oil content of seeds. For instance, for processed oilseeds such as soy and canola, increasing the absolute oil content of the seed will increase the value of such grains. For processed corn it may be desired to either increase or decrease oil content, depending on utilization of other major constituents. Decreasing oil may improve the quality of isolated starch by reducing undesired flavors associated with oil oxidation. Alternatively, in ethanol production, where flavor is unimportant, increasing oil content may increase overall value. In many feed grains, such as corn and wheat, it is desirable to increase seed oil content, because oil has higher energy content than other seed constituents such as carbohydrate. Oilseed processing, like most grain processing businesses, is a capital-intensive business; thus small shifts in the distribution of products from the low valued components to the high value oil component can have substantial economic impacts for grain processors.

Biotechnological manipulation of oils can provide compositional alteration and improvement of oil yield. Compositional alterations include high oleic soybean and corn oil (U.S. Pat. Nos. 6,229,033 and 6,248,939), and laurate-containing seeds (U.S. Pat. No. 5,639,790), among others. Work in compositional alteration has predominantly focused on processed oilseeds but has been readily extendable to non-oilseed crops, including corn. While there is considerable interest in increasing oil content, the only currently practiced biotechnology in this area is High-Oil Corn (HOC) technology (DuPont, U.S. Pat. No. 5,704,160). HOC employs high oil pollinators developed by classical selection breeding along with elite (male-sterile) hybrid females in a production system referred to as TopCross. The TopCross High Oil system raises harvested grain oil content in maize from about 3.5% to about 7%, improving the energy content of the grain.

While it has been fruitful, the HOC production system has inherent limitations. First, the system of having a low percentage of pollinators responsible for an entire field's seed set contains inherent risks, particularly in drought years. Second, oil contents in current HOC fields have plateaued at about 9% oil. Finally, high-oil corn is not primarily a biochemical change, but rather an anatomical mutant (increased embryo size) that has the indirect result of increasing oil content. For these reasons, an alternative high oil strategy, particularly one that derives from an altered biochemical output, would be especially valuable.

The most obvious target crops for the processed oil market are soy and rapeseed, and a large body of commercial work (e.g., U.S. Pat. No. 5,952,544; PCT application WO9411516) demonstrates that *Arabidopsis* is an excellent model for oil metabolism in these crops. Biochemical screens of seed oil composition have identified *Arabidopsis* genes for many critical biosynthetic enzymes and have led to identification of agronomically important gene orthologs. For instance, screens using chemically mutagenized populations have identified lipid mutants whose seeds display altered fatty acid composition (Lernieux et al., 1990; James and Dooner, 1990). T-DNA mutagenesis screens (Feldnann et al., 1989) that detected altered fatty acid composition identified the omega 3 desaturase (FAD3) and delta-12 desaturase (FAD2) genes (U.S. Pat. No. 5,952,544; Yadav et al., 1993; Okuley et al., 1994). A screen which focused on oil content rather than oil quality, analyzed chemically-induced mutants for wrinkled seeds or altered seed density, from which altered seed oil content was inferred (Focks and Benning, 1998). Another screen, designed to identify enzymes involved in production of very long chain fatty acids, identified a mutation in the gene encoding a diacylglycerol acyltransferase (DGAT) as being responsible for reduced triacyl glycerol accumulation in seeds (Katavic V et al, 1995). It was further shown that seed-specific over-expression of the DGAT cDNA was associated with increased seed oil content (Jako et al., 2001).

Activation tagging in plants refers to a method of generating random mutations by insertion of a heterologous nucleic acid construct comprising regulatory sequences (e.g., an enhancer) into a plant genome. The regulatory sequences can act to enhance transcription of one or more native plant genes; accordingly, activation tagging is a fruitful method for generating gain-of-function, generally dominant mutants (see, e.g., Hayashi et al., 1992; Weigel D et al. 2000). The inserted construct provides a molecular tag for rapid identification of the native plant whose mis-expression causes the mutant phenotype. Activation tagging may also cause loss-of-function phenotypes. The insertion may result in disruption of a native plant gene, in which case the phenotype is generally recessive.

Activation tagging has been used in various species, including tobacco and *Arabidopsis*, to identify many different kinds of mutant phenotypes and the genes associated with these phenotypes (Wilson et al., 1996, Schaffer et al., 1998, Fridborg et al., 1999; Kardailsky et al., 1999; Christensen S et al., 1998).

SUMMARY OF THE INVENTION

The invention provides a transgenic plant having a high oil phenotype. The transgenic plant comprises a transformation vector comprising a nucleotide sequence that encodes or is complementary to a sequence that encodes a HIO128.5 polypeptide. In preferred embodiments, the transgenic plant is selected from the group consisting of rapeseed, soy, corn, sunflower, cotton, cocoa, safflower, oil palm, coconut palm, flax, castor and peanut. The invention further provides a method of producing oil comprising growing the transgenic plant and recovering oil from said plant.

The invention also provides a transgenic plant cell having a high oil phenotype. The transgenic plant cell comprises a transformation vector comprising a nucleotide sequence that encodes or is complementary to a sequence that encodes a High Oil (hereinafter "HIO128.5") polypeptide. In preferred embodiments, the transgenic plant cell is selected from the group consisting of rapeseed, soy, corn, sunflower, cotton, cocoa, safflower, oil palm, coconut palm, flax, castor and peanut. In other embodiments, the plant cell is a seed, pollen, propagule, or embryo cell. The invention further provides feed, meal, grain, food, or seed comprising a nucleic acid sequence that encodes a HIO128.5 polypeptide. The invention also provides feed, meal, grain, food, or seed comprising the HIO128.5 polypeptide, or an ortholog thereof.

The transgenic plant of the invention is produced by a method that comprises introducing into progenitor cells of the plant a plant transformation vector comprising a nucleotide sequence that encodes or is complementary to a sequence that encodes a HIO128.5 polypeptide, and growing the transformed progenitor cells to produce a transgenic plant, wherein the HIO128.5 polynucleotide sequence is expressed causing the high oil phenotype. In other embodiments, the invention provides a plant that is the direct progeny or the indirect progeny of a plant grown from said progenitor cells. The invention further provides plant cells obtained from said transgenic plant. The invention also provides plant cells from a plant that is the direct progeny or the indirect progeny of a plant grown from said progenitor cells.

The present invention also provides a container of over about 10,000, more preferably about 20,000, and even more preferably about 40,000 seeds where over about 10%, more preferably about 25%, more preferably about 50%, and even more preferably about 75% or more preferably about 90% of the seeds are seeds derived from a plant of the present invention.

The present invention also provides a container of over about 10 kg, more preferably about 25 kg, and even more preferably about 50 kg seeds where over about 10%, more preferably about 25%, more preferably about 50%, and even more preferably about 75% or more preferably about 90% of the seeds are seeds derived from a plant of the present invention.

Any of the plants or parts thereof of the present invention may be processed to produce a feed, food, meal, or oil preparation. A particularly preferred plant part for this purpose is a seed. In a preferred embodiment the feed, food, meal, or oil preparation is designed for ruminant animals. Methods to produce feed, food, meal, and oil preparations are known in the art. See, for example, U.S. Pat. Nos. 4,957,748; 5,100,679; 5,219,596; 5,936,069; 6,005,076; 6,146,669; and 6,156,227. The meal of the present invention may be blended with other meals. In a preferred embodiment, the meal produced from plants of the present invention or generated by a method of the present invention constitutes greater than about 0.5%, about 1%, about 5%, about 10%, about 25%, about 50%, about 75%, or about 90% by volume or weight of the meal component of any product. In another embodiment, the meal preparation may be blended and can constitute greater than about 10%, about 25%, about 35%, about 50%, or about 75% of the blend by volume.

DETAILED DESCRIPTION OF THE INVENTION

Definitions

Unless otherwise indicated, all technical and scientific terms used herein have the same meaning as they would to one skilled in the art of the present invention. Practitioners are particularly directed to Sambrook et al., 1989, and Ausubel F M et al., 1993, for definitions and terms of the art. It is to be understood that this invention is not limited to the particular methodology, protocols, and reagents described, as these may vary.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

A "heterologous" nucleic acid construct or sequence has a portion of the sequence that is not native to the plant cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell, by infection, transfection, microinjection, electroporation, or the like. A "heterologous" nucleic acid construct may contain a control sequence/DNA coding sequence combination that is the same as, or different from a control sequence/DNA coding sequence combination found in the native plant.

As used herein, the term "gene" means the segment of DNA involved in producing a polypeptide chain, which may or may not include regions preceding and following the coding region, e.g. 5' untranslated (5' UTR) or "leader" sequences and 3' UTR or "trailer" sequences, as well as intervening sequences (introns) between individual coding segments (exons) and non-transcribed regulatory sequence.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

As used herein, the term "gene expression" refers to the process by which a polypeptide is produced based on the nucleic acid sequence of a gene. The process includes both transcription and translation; accordingly, "expression" may refer to either a polynucleotide or polypeptide sequence, or both. Sometimes, expression of a polynucleotide sequence will not lead to protein translation. "Over-expression" refers to increased expression of a polynucleotide and/or polypeptide sequence relative to its expression in a wild-type (or other reference [e.g., non-transgenic]) plant and may relate to a naturally-occurring or non-naturally occurring sequence. "Ectopic expression" refers to expression at a time, place, and/or increased level that does not naturally occur in the non-altered or wild-type plant. "Under-expression" refers to decreased expression of a polynucleotide and/or polypeptide sequence, generally of an endogenous gene, relative to its expression in a wild-type plant. The terms "mis-expression" and "altered expression" encompass over-expression, under-expression, and ectopic expression.

The term "introduced" in the context of inserting a nucleic acid sequence into a cell, means "transfection", or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

As used herein, a "plant cell" refers to any cell derived from a plant, including cells from undifferentiated tissue (e.g., callus) as well as plant seeds, pollen, progagules and embryos.

As used herein, the terms "native" and "wild-type" relative to a given plant trait or phenotype refers to the form in which that trait or phenotype is found in the same variety of plant in nature.

As used herein, the term "modified" regarding a plant trait, refers to a change in the phenotype of a transgenic plant relative to the similar non-transgenic plant. An "interesting phenotype (trait)" with reference to a transgenic plant refers to an observable or measurable phenotype demonstrated by a T1 and/or subsequent generation plant, which is not displayed by the corresponding non-transgenic (i.e., a genotypically similar plant that has been raised or assayed under similar conditions). An interesting phenotype may represent an improvement in the plant or may provide a means to produce improvements in other plants. An "improvement" is a feature that may enhance the utility of a plant species or variety by providing the plant with a unique and/or novel quality. An "altered oil content phenotype" refers to measurable phenotype of a genetically modified plant, where the plant displays a statistically significant increase or decrease in overall oil content (i.e., the percentage of seed mass that is oil), as compared to the similar, but non-modified plant. A high oil phenotype refers to an increase in overall oil content.

As used herein, a "mutant" polynucleotide sequence or gene differs from the corresponding wild type polynucleotide sequence or gene either in terms of sequence or expression, where the difference contributes to a modified plant phenotype or trait. Relative to a plant or plant line, the term "mutant" refers to a plant or plant line which has a modified plant phenotype or trait, where the modified phenotype or trait is associated with the modified expression of a wild type polynucleotide sequence or gene.

As used herein, the term "T1" refers to the generation of plants from the seed of T0 plants. The T1 generation is the first set of transformed plants that can be selected by application of a selection agent, e.g., an antibiotic or herbicide, for which the transgenic plant contains the corresponding resistance gene. The term "T2" refers to the generation of plants by self-fertilization of the flowers of T1 plants, previously selected as being transgenic. T3 plants are generated from T2 plants, etc. As used herein, the "direct progeny" of a given plant derives from the seed (or, sometimes, other tissue) of that plant and is in the immediately subsequent generation; for instance, for a given lineage, a T2 plant is the direct progeny of a T1 plant. The "indirect progeny" of a given plant derives from the seed (or other tissue) of the direct progeny of that plant, or from the seed (or other tissue) of subsequent generations in that lineage; for instance, a T3 plant is the indirect progeny of a T1 plant.

As used herein, the term "plant part" includes any plant organ or tissue, including, without limitation, seeds, embryos, meristematic regions, callus tissue, leaves, roots, shoots, gametophytes, sporophytes, pollen, and microspores. Plant cells can be obtained from any plant organ or tissue and cultures prepared therefrom. The class of plants which can be used in the methods of the present invention is generally as broad as the class of higher plants amenable to transformation techniques, including both monocotyledenous and dicotyledenous plants.

As used herein, "transgenic plant" includes a plant that comprises within its genome a heterologous polynucleotide. The heterologous polynucleotide can be either stably integrated into the genome, or can be extra-chromosomal. Preferably, the polynucleotide of the present invention is stably integrated into the genome such that the polynucleotide is passed on to successive generations. A plant cell, tissue, organ, or plant into which the heterologous polynucleotides have been introduced is considered "transformed", "transfected", or "transgenic". Direct and indirect progeny of transformed plants or plant cells that also contain the heterologous polynucleotide are also considered transgenic.

Various methods for the introduction of a desired polynucleotide sequence encoding the desired protein into plant cells are available and known to those of skill in the art and include, but are not limited to: (1) physical methods such as microinjection, electroporation, and microprojectile mediated delivery (biolistics or gene gun technology); (2) virus mediated delivery methods; and (3) *Agrobacterium*-mediated transformation methods.

The most commonly used methods for transformation of plant cells are the *Agrobacterium*-mediated DNA transfer process and the biolistics or microprojectile bombardment mediated process (i.e., the gene gun). Typically, nuclear transformation is desired but where it is desirable to specifically transform plastids, such as chloroplasts or amyloplasts, plant plastids may be transformed utilizing a microprojectile-mediated delivery of the desired polynucleotide.

*Agrobacterium*-mediated transformation is achieved through the use of a genetically engineered soil bacterium belonging to the genus *Agrobacterium*. A number of wild-type and disarmed strains of *Agrobacterium tumefaciens* and *Agrobacterium rhizogenes* harboring Ti or Ri plasmids can be used for gene transfer into plants. Gene transfer is done via the transfer of a specific DNA known as "T-DNA" that can be genetically engineered to carry any desired piece of DNA into many plant species.

*Agrobacterium*-mediated genetic transformation of plants involves several steps. The first step, in which the virulent *Agrobacterium* and plant cells are first brought into contact with each other, is generally called "inoculation". Following the inoculation, the *Agrobacterium* and plant cells/tissues are permitted to be grown together for a period of several hours to several days or more under conditions suitable for growth and T-DNA transfer. This step is termed "co-culture". Following co-culture and T-DNA delivery, the plant cells are treated with bactericidal or bacteriostatic agents to kill the *Agrobacterium* remaining in contact with the explant and/or in the vessel containing the explant. If this is done in the absence of any selective agents to promote preferential growth of transgenic versus non-transgenic plant cells, then this is typically referred to as the "delay" step. If done in the presence of selective pressure favoring transgenic plant cells, then it is referred to as a "selection" step. When a "delay" is used, it is typically followed by one or more "selection" steps.

With respect to microprojectile bombardment (U.S. Pat. No. 5,550,318 (Adams et al.); U.S. Pat. No. 5,538,880 (Lundquist et. al.), U.S. Pat. No. 5,610,042 (Chang et al.); and PCT Publication WO 95/06128 (Adams et al.); each of which is specifically incorporated herein by reference in its entirety), particles are coated with nucleic acids and delivered into cells by a propelling force. Exemplary particles include those comprised of tungsten, platinum, and preferably, gold.

An illustrative embodiment of a method for delivering DNA into plant cells by acceleration is the Biolistics Particle Delivery System (BioRad, Hercules, Calif.), which can be used to propel particles coated with DNA or cells through a screen, such as a stainless steel or Nytex screen, onto a filter surface covered with monocot plant cells cultured in suspension.

Microprojectile bombardment techniques are widely applicable, and may be used to transform virtually any plant species. Examples of species that have been transformed by microprojectile bombardment include monocot species such as maize (International Publication No. WO 95/06128 (Adams et al.)), barley, wheat (U.S. Pat. No. 5,563,055 (Townsend et al.) incorporated herein by reference in its entirety), rice, oat, rye, sugarcane, and sorghum; as well as a number of dicots including tobacco, soybean (U.S. Pat. No. 5,322,783 (Tomes et al.), incorporated herein by reference in its entirety), sunflower, peanut, cotton, tomato, and legumes in general (U.S. Pat. No. 5,563,055 (Townsend et al.) incorporated herein by reference in its entirety).

To select or score for transformed plant cells regardless of transformation methodology, the DNA introduced into the cell contains a gene that functions in a regenerable plant tissue to produce a compound that confers upon the plant tissue resistance to an otherwise toxic compound. Genes of interest for use as a selectable, screenable, or scorable marker would include but are not limited to GUS, green fluorescent protein (GFP), luciferase (LUX), antibiotic or herbicide tolerance genes. Examples of antibiotic resistance genes include the penicillins, kanamycin (and neomycin, G418, bleomycin); methotrexate (and trimethoprim); chloramphenicol; kanamycin and tetracycline. Polynucleotide molecules encoding proteins involved in herbicide tolerance are known in the art, and include, but are not limited to a polynucleotide molecule encoding 5-enolpyruvylshikimate-3-phosphate synthase (EPSPS) described in U.S. Pat. No. 5,627,061 (Barry, et al.), U.S. Pat. No. 5,633,435 (Barry, et al.), and U.S. Pat. No. 6,040,497 (Spencer, et al.) and aroA described in U.S. Pat. No. 5,094,945 (Comai) for glyphosate tolerance; a polynucleotide molecule encoding bromoxynil nitrilase (Bxn) described in U.S. Pat. No. 4,810,648 (Duerrschnabel, et al.) for Bromoxynil tolerance; a polynucleotide molecule encoding phytoene desaturase (crtI) described in Misawa et al, (1993) Plant J. 4:833-840 and Misawa et al, (1994) Plant J. 6:481-489 for norflurazon tolerance; a polynucleotide molecule encoding acetohydroxyacid synthase (AHAS, aka ALS) described in Sathasiivan et al. (1990) Nucl. Acids Res. 18:2188-2193 for tolerance to sulfonylurea herbicides; and the bar gene described in DeBlock, et al. (1987) EMBO J. 6:2513-2519 for glufosinate and bialaphos tolerance.

The regeneration, development, and cultivation of plants from various transformed explants are well documented in the art. This regeneration and growth process typically includes the steps of selecting transformed cells and culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Cells that survive the exposure to the selective agent, or cells that have been scored positive in a screening assay, may be cultured in media that supports regeneration of plants. Developing plantlets are transferred to soil less plant growth mix, and hardened off, prior to transfer to a greenhouse or growth chamber for maturation.

The present invention can be used with any transformable cell or tissue. By transformable as used herein is meant a cell or tissue that is capable of further propagation to give rise to a plant. Those of skill in the art recognize that a number of plant cells or tissues are transformable in which after insertion of exogenous DNA and appropriate culture conditions the plant cells or tissues can form into a differentiated plant. Tissue suitable for these purposes can include but is not limited to immature embryos, scutellar tissue, suspension cell cultures, immature inflorescence, shoot meristem, nodal explants, callus tissue, hypocotyl tissue, cotyledons, roots, and leaves.

Any suitable plant culture medium can be used. Examples of suitable media would include but are not limited to MS-based media (Murashige and Skoog, Physiol. Plant, 15:473-497, 1962) or N6-based media (Chu et al., Scientia Sinica 18:659, 1975) supplemented with additional plant growth regulators including but not limited to auxins, cytokinins, ABA, and gibberellins. Those of skill in the art are familiar with the variety of tissue culture media, which when supplemented appropriately, support plant tissue growth and development and are suitable for plant transformation and regeneration. These tissue culture media can either be purchased as a commercial preparation, or custom prepared and modified. Those of skill in the art are aware that media and media supplements such as nutrients and growth regulators for use in transformation and regeneration and other culture conditions such as light intensity during incubation, pH, and incubation temperatures that can be optimized for the particular variety of interest.

One of ordinary skill will appreciate that, after an expression cassette is stably incorporated in transgenic plants and confirmed to be operable, it can be introduced into other plants by sexual crossing. Any of a number of standard breeding techniques can be used, depending upon the species to be crossed.

Identification of Plants with an Altered Oil Content Phenotype

We used an *Arabidopsis* activation tagging (ACTTAG) screen to identify the association between the gene we have designated "HIO128.5," (At5g37780; GI#30693152) encoding one or more calmodulin 4 proteins (synonym: T31G3.3; GI#15240343), and an altered oil content phenotype (specifically, a high oil phenotype). Briefly, and as further described in the Examples, a large number of *Arabidopsis* plants were mutated with the pSKI015 vector, which comprises a T-DNA from the Ti plasmid of *Agrobacterium tumifaciens*, a viral enhancer element, and a selectable marker gene (Weigel et al., 2000). When the T-DNA inserts into the genome of transformed plants, the enhancer element can cause up-regulation of genes in the vicinity, generally within about 10 kilobase (kb) of the enhancer. T1 plants were exposed to the selective agent in order to specifically recover transformed plants. To amplify the seed stocks, about eighteen seeds from the T1 plants were sown in soil and, after germination, exposed to the selective agent to recover transformed T2 plants. T3 seed from these plants was harvested and pooled. Oil content of the seed was estimated using Near Infrared Spectroscopy (NIR) as described in Example 1.

An *Arabidopsis* line that showed a high-oil phenotype was identified wherein oil content (i.e., fatty acids) constituted about 39.2% compared to a flat average oil content of 35.2% for seed from other plants planted on that day (a 11% increase in oil). The association of the HIO128.5 gene with the high oil phenotype was discovered by analysis of the genomic DNA sequence flanking the T-DNA insertion in the identified line. Accordingly, HIO128.5 genes and/or polypeptides may be employed in the development of genetically modified plants having a modified oil content phenotype ("a HIO128.5 phenotype"). HIO128.5 genes may be used in the generation of oilseed crops that provide improved oil yield from oilseed processing and in the generation of feed grain crops that provide increased energy for animal feeding. HIO128.5 genes may further be used to increase the oil content of specialty oil crops, in order to augment yield of desired unusual fatty acids. Transgenic plants that have been genetically modified to express HIO128.5 can be used in the production of oil, wherein the transgenic plants are grown, and oil is obtained from plant parts (e.g. seed) using standard methods.

HIO128.5 Nucleic Acids and Polypeptides

Arabidopsis HIO128.5 nucleic acid (genomic DNA) sequence is provided in SEQ ID NO: 1 and in Genbank entry GI#30693152. The corresponding protein sequence is provided in SEQ ID NO:2 and in GI#15240343. Nucleic acids and/or proteins that are orthologs or paralogs of Arabidopsis HIO128.5, are described in Example 3 below.

As used herein, the term "HIO128.5 polypeptide" refers to a full-length HIO128.5 protein or a fragment, derivative (variant), or ortholog thereof that is "functionally active," meaning that the protein fragment, derivative, or ortholog exhibits one or more or the functional activities associated with the polypeptide of SEQ ID NO:2. In one preferred embodiment, a functionally active HIO128.5 polypeptide causes an altered oil content phenotype when mis-expressed in a plant. In a further preferred embodiment, mis-expression of the HIO128.5 polypeptide causes a high oil phenotype in a plant. In another embodiment, a functionally active HIO128.5 polypeptide is capable of rescuing defective (including deficient) endogenous HIO128.5 activity when expressed in a plant or in plant cells; the rescuing polypeptide may be from the same or from a different species as that with defective activity. In another embodiment, a functionally active fragment of a full length HIO128.5 polypeptide (i.e., a native polypeptide having the sequence of SEQ ID NO:2 or a naturally occurring ortholog thereof) retains one of more of the biological properties associated with the full-length HIO128.5 polypeptide, such as signaling activity, binding activity, catalytic activity, or cellular or extra-cellular localizing activity. A HIO128.5 fragment preferably comprises a HIO128.5 domain, such as a C- or N-terminal or catalytic domain, among others, and preferably comprises at least 10, preferably at least 20, more preferably at least 25, and most preferably at least 50 contiguous amino acids of a HIO1128.5 protein. Functional domains can be identified using the PFAM program (Bateman A et al., 1999 Nucleic Acids Res 27:260-262). A preferred HIO128.5 fragment comprises of cone or more calmodulin 4 proteins.

Functionally active variants of full-length HIO128.5 polypeptides or fragments thereof include polypeptides with amino acid insertions, deletions, or substitutions that retain one of more of the biological properties associated with the full-length HIO128.5 polypeptide. In some cases, variants are generated that change the post-translational processing of a HIO128.5 polypeptide. For instance, variants may have altered protein transport or protein localization characteristics or altered protein half-life compared to the native polypeptide.

As used herein, the term "HIO128.5 nucleic acid" encompasses nucleic acids with the sequence provided in or complementary to the sequence provided in SEQ ID NO:1, as well as functionally active fragments, derivatives, or orthologs thereof. A HIO128.5 nucleic acid of this invention may be DNA, derived from genomic DNA or cDNA, or RNA.

In one embodiment, a functionally active HIO128.5 nucleic acid encodes or is complementary to a nucleic acid that encodes a functionally active HIO128.5 polypeptide. Included within this definition is genomic DNA that serves as a template for a primary RNA transcript (i.e., an mRNA precursor) that requires processing, such as splicing, before encoding the functionally active HIO128.5 polypeptide. A HIO128.5 nucleic acid can include other non-coding sequences, which may or may not be transcribed; such sequences include 5' and 3' UTRs, polyadenylation signals and regulatory sequences that control gene expression, among others, as are known in the art. Some polypeptides require processing events, such as proteolytic cleavage, covalent modification, etc., in order to become fully active. Accordingly, functionally active nucleic acids may encode the mature or the pre-processed HIO128.5 polypeptide, or an intermediate form. A HIO128.5 polynucleotide can also include heterologous coding sequences, for example, sequences that encode a marker included to facilitate the purification of the fused polypeptide, or a transformation marker.

In another embodiment, a functionally active HIO128.5 nucleic acid is capable of being used in the generation of loss-of-function HIO128.5 phenotypes, for instance, via antisense suppression, co-suppression, etc.

In one preferred embodiment, a HIO128.5 nucleic acid used in the methods of this invention comprises a nucleic acid sequence that encodes or is complementary to a sequence that encodes a HIO128.5 polypeptide having at least 50%, 60%, 70%, 75%, 80%, 85%, 90%, 95% or more sequence identity to the polypeptide sequence presented in SEQ ID NO:2.

In another embodiment a HIO128.5 polypeptide of the invention comprises a polypeptide sequence with at least 50% or 60% identity to the HIO128.5 polypeptide sequence of SEQ ID NO:2, and may have at least 70%, 80%, 85%, 90% or 95% or more sequence identity to the HIO128.5 polypeptide sequence of SEQ ID NO:2, such as one or more calmodulin 4 proteins. In another embodiment, a HIO128.5 polypeptide comprises a polypeptide sequence with at least 50%, 60%, 70%, 80%, 85%, 90% or 95% or more sequence identity to a functionally active fragment of the polypeptide presented in SEQ ID NO:2. In yet another embodiment, a HIO128.5 polypeptide comprises a polypeptide sequence with at least 50%, 60%, 70%, 80%, or 90% identity to the polypeptide sequence of SEQ ID NO:2 over its entire length and comprises of one or more calmodulin 4 proteins.

In another aspect, a HIO128.5 polynucleotide sequence is at least 50% to 60% identical over its entire length to the HIO128.5 nucleic acid sequence presented as SEQ ID NO:1, or nucleic acid sequences that are complementary to such a HIO128.5 sequence, and may comprise at least 70%, 80%, 85%, 90% or 95% or more sequence identity to the HIO128.5 sequence presented as SEQ ID NO:1 or a functionally active fragment thereof, or complementary sequences.

As used herein, "percent (%) sequence identity" with respect to a specified subject sequence, or a specified portion thereof, is defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. (1990) 215:403-410) with search parameters set to default values. The HSP S and HSP S2 parameters are dynamic values and are established by the program itself depending upon the composition of the particular sequence and composition of the particular database against which the sequence of interest is being searched. A "% identity value" is determined by the number of matching identical nucleotides or amino acids divided by the sequence length for which the percent identity is being reported. "Percent (%) amino acid sequence similarity" is determined by doing the same calculation as for determining % amino acid sequence identity, but including conservative amino acid substitutions in addition to identical amino acids in the computation. A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine and glycine.

Derivative nucleic acid molecules of the subject nucleic acid molecules include sequences that selectively hybridize to the nucleic acid sequence of SEQ ID NO:1. The stringency of hybridization can be controlled by temperature, ionic strength, pH, and the presence of denaturing agents such as formamide during hybridization and washing. Conditions routinely used are well known (see, e.g., Current Protocol in Molecular Biology, Vol. 1, Chap. 2.10, John Wiley & Sons, Publishers (1994); Sambrook et al., Molecular Cloning, Cold Spring Harbor (1989)). In some embodiments, a nucleic acid molecule of the invention is capable of hybridizing to a nucleic acid molecule containing the nucleotide sequence of SEQ ID NO:1 under stringent hybridization conditions that are: prehybridization of filters containing nucleic acid for 8 hours to overnight at 65° C. in a solution comprising 6× single strength citrate (SSC) (1×SSC is 0.15 M NaCl, 0.015 M Na citrate; pH 7.0), 5×Denhardt's solution, 0.05% sodium pyrophosphate and 100 µg/ml herring sperm DNA; hybridization for 18-20 hours at 65° C. in a solution containing 6×SSC, 1×Denhardt's solution, 100 µg/ml yeast tRNA and 0.05% sodium pyrophosphate; and washing of filters at 65° C. for 1 h in a solution containing 0.1×SSC and 0.1% SDS (sodium dodecyl sulfate). In other embodiments, moderately stringent hybridization conditions are used that are: pretreatment of filters containing nucleic acid for 6 h at 40° C. in a solution containing 35% formamide, 5×SSC, 50 mM Tris-HCl (pH 7.5), 5 µM EDTA, 0.1% PVP, 0.1% Ficoll, 1% BSA, and 500 µg/ml denatured salmon sperm DNA; hybridization for 18-20 h at 40° C. in a solution containing 35% formamide, 5×SSC, 50 mM Tris-HCl (pH 7.5), 5 mM EDTA, 0.02% PVP, 0.02% Ficoll, 0.2% BSA, 100 µg/ml salmon sperm DNA, and 10% (wt/vol) dektran sulfate; followed by washing twice for 1 hour at 55° C. in a solution containing 2×SSC and 0.1% SDS. Alternatively, low stringency conditions can be used that comprise: incubation for 8 hours to overnight at 37° C. in a solution comprising 20% formamide, 5×SSC, 50 mM sodium phosphate (pH 7.6), 5×Denhardt's solution, 10% dextran sulfate, and 20 µg/ml denatured sheared salmon sperm DNA; hybridization in the same buffer for 18 to 20 hours; and washing of filters in 1×SSC at about 37° C. for 1 hour.

As a result of the degeneracy of the genetic code, a number of polynucleotide sequences encoding a HIO128.5 polypeptide can be produced. For example, codons may be selected to increase the rate at which expression of the polypeptide occurs in a particular host species, in accordance with the optimum codon usage dictated by the particular host organism (see, e.g., Nakamura et al, 1999). Such sequence variants may be used in the methods of this invention.

The methods of the invention may use orthologs of the Arabidopsis HIO128.5. Methods of identifying the orthologs in other plant species are known in the art. Normally, orthologs in different species retain the same function, due to presence of one or more protein motifs and/or 3-dimensional structures. In evolution, when a gene duplication event follows speciation, a single gene in one species, such as Arabidopsis, may correspond to multiple genes (paralogs) in another. As used herein, the term "orthologs" encompasses paralogs. When sequence data is available for a particular plant species, orthologs are generally identified by sequence homology analysis, such as BLAST analysis, usually using protein bait sequences. Sequences are assigned as a potential ortholog if the best hit sequence from the forward BLAST result retrieves the original query sequence in the reverse BLAST (Huynen M A and Bork P, Proc Natl Acad Sci (1998) 95:5849-5856; Huynen M A et al., Genome Research (2000) 10:1204-1210).

Programs for multiple sequence alignment, such as CLUSTAL (Thompson J D et al, 1994, Nucleic Acids Res 22:4673-4680) may be used to highlight conserved regions and/or residues of orthologous proteins and to generate phylogenetic trees. In a phylogenetic tree representing multiple homologous sequences from diverse species (e.g., retrieved through BLAST analysis), orthologous sequences from two species generally appear closest on the tree with respect to all other sequences from these two species. Structural threading or other analysis of protein folding (e.g., using software by ProCeryon, Biosciences, Salzburg, Austria) may also identify potential orthologs. Nucleic acid hybridization methods may also be used to find orthologous genes and are preferred when sequence data are not available. Degenerate PCR and screening of cDNA or genomic DNA libraries are common methods for finding related gene sequences and are well known in the art (see, e.g., Sambrook, 1989; Dieffenbach and Dveksler, 1995). For instance, methods for generating a cDNA library front the plant species of interest and probing the library with partially homologous gene probes are described in Sambrook et al. A highly conserved portion of the Arabidopsis HIO128.5 coding sequence may be used as a probe. HIO128.5 ortholog nucleic acids may hybridize to the nucleic acid of SEQ ID NO:1 under high, moderate, or low stringency conditions. After amplification or isolation of a segment of a putative ortholog, that segment may be cloned and sequenced by standard techniques and utilized as a probe to isolate a complete cDNA or genomic clone. Alternatively, it is possible to initiate an EST project to generate a database of sequence information for the plant species of interest. In another approach, antibodies that specifically bind known HIO128.5 polypeptides are used for ortholog isolation (see, e.g., Harlow and Lane, 1988, 1999). Western blot analysis can determine that a HIO128.5 ortholog (i.e., an orthologous protein) is present in a crude extract of a particular plant species. When reactivity is observed, the sequence encoding the candidate ortholog may be isolated by screening expression libraries representing the particular plant species. Expression libraries can be constructed in a variety of commercially available vectors, including lambda gt11, as described in Sambrook, et al., 1989. Once the candidate ortholog(s) are identified by any of these means, candidate orthologous sequence are used as bait (the "query") for the reverse BLAST against sequences from Arabidopsis or other species in which HIO128.5 nucleic acid and/or polypeptide sequences have been identified.

HIO128.5 nucleic acids and polypeptides may be obtained using any available method. For instance, techniques for isolating cDNA or genomic DNA sequences of interest by screening DNA libraries or by using polymerase chain reaction (PCR), as previously described, are well known in the art. Alternatively, nucleic acid sequence may be synthesized. Any known method, such as site directed mutagenesis (Kunkel T A et al., 1991), may be used to introduce desired changes into a cloned nucleic acid.

In general, the methods of the invention involve incorporating the desired form of the HIO128.5 nucleic acid into a plant expression vector for transformation of plant cells, and the HIO128.5 polypeptide is expressed in the host plant. An isolated HIO128.5 nucleic acid molecule is other than in the form or setting in which it is found in nature and is identified and separated from least one contaminant nucleic acid molecule with which it is ordinarily associated in the natural source of the HIO128.5 nucleic acid. However, an isolated HIO128.5 nucleic acid molecule includes HIO128.5 nucleic acid molecules contained in cells that ordinarily express HIO128.5 where, for example, the nucleic acid molecule is in a chromosomal location different from that of natural cells.

Generation of Genetically Modified Plants with an Altered Oil Content Phenotype

HIO128.5 nucleic acids and polypeptides may be used in the generation of genetically modified plants having a modified oil content phenotype. As used herein, a "modified oil content phenotype" may refer to modified oil content in any part of the plant; the modified oil content is often observed in seeds. In a preferred embodiment, altered expression of the HIO128.5 gene in a plant is used to generate plants with a high oil phenotype.

The methods described herein are generally applicable to all plants. Although activation tagging and gene identification is carried out in *Arabidopsis*, the HIO128.5 gene (or an ortholog, variant or fragment thereof) may be expressed in any type of plant. In a preferred embodiment, the invention is directed to oil-producing plants, which produce and store triacylglycerol in specific organs, primarily in seeds. Such species include soybean (*Glycine max*), rapeseed and canola (including *Brassica napus, B. campestris*), sunflower (*Heliantzus annus*), cotton (*Gossypiumn hirsutum*), corn (*Zea mays*), cocoa (*Theobroma cacao*), safflower (*Carthamus tinctorius*), oil palm (*Elaeis guineensis*), coconut palm (*Cocos niucifera*), flax (*Linum usitatissimum*), castor (*Ricinus communis*) and peanut (*Arachis hypogaea*). The invention may also be directed to fruit- and vegetable-bearing plants, grain-producing plants, nut-producing plants, rapid cycling *Brassica* species, alfalfa (*Medicago sativa*), tobacco (Nicotiana), turfgrass (Poaceae family), other forage crops, and wild species that may be a source of unique fatty acids.

The skilled artisan will recognize that a wide variety of transformation techniques exist in the art, and new techniques are continually becoming available. Any technique that is suitable for the target host plant can be employed within the scope of the present invention. For example, the constructs can be introduced in a variety of forms including, but not limited to as a strand of DNA, in a plasmid, or in an artificial chromosome. The introduction of the constructs into the target plant cells can be accomplished by a variety of techniques, including, but not limited to *Agrobacterium*-mediated transformation, electroporation, microinjection, microprojectile bombardment calcium-phosphate-DNA co-precipitation or liposome-mediated transformation of a heterologous nucleic acid. The transformation of the plant is preferably permanent, i.e. by integration of the introduced expression constructs into the host plant genome, so that the introduced constructs are passed onto successive plant generations. Depending upon the intended use, a heterologous nucleic acid construct comprising a HIO128.5 polynucleotide may encode the entire protein or a biologically active portion thereof.

In one embodiment, binary Ti-based vector systems may be used to transfer polynucleotides. Standard *Agrobacterium* binary vectors are known to those of skill in the art, and many are commercially available (e.g., pBI121 Clontech Laboratories, Palo Alto, Calif.). A construct or vector may include a plant promoter to express the nucleic acid molecule of choice. In a preferred embodiment, the promoter is a plant promoter.

The optimal procedure for transformation of plants with *Agrobacterium* vectors will vary with the type of plant being transformed. Exemplary methods for *Agrobacterium*-mediated transformation include transformation of explants of hypocotyl, shoot tip, stem or leaf tissue, derived from sterile seedlings and/or plantlets. Such transformed plants may be reproduced sexually, or by cell or tissue culture. *Agrobacterium* transformation has been previously described for a large number of different types of plants and methods for such transformation may be found in the scientific literature. Of particular relevance are methods to transform commercially important crops, such as rapeseed (De Block et al., 1989), sunflower (Everett et al., 1987), and soybean (Christou et al., 1989; Kline et al., 1987).

Expression (including transcription and translation) of HIO128.5 may be regulated with respect to the level of expression, the tissue type(s) where expression takes place and/or developmental stage of expression. A number of heterologous regulatory sequences (e.g., promoters and enhancers) are available for controlling the expression of a HIO128.5 nucleic acid. These include constitutive, inducible and regulatable promoters, as well as promoters and enhancers that control expression in a tissue- or temporal-specific manner. Exemplary constitutive promoters include the raspberry E4 promoter (U.S. Pat. Nos. 5,783,393 and 5,783,394), the nopaline synthase (NOS) promoter (Ebert et al., *Proc. Natl. Acad. Sci. (U.S.A.)* 84:5745-5749, 1987), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et al., *Plant Mol. Biol.* 9:315-324, 1987) and the CaMV 35S promoter (Odell et al., *Nature* 313:810-812, 1985 and Jones JD et al, 1992), the melon actin promoter (published PCT application WO0056863), the figwort mosaic virus 35S-promoter (U.S. Pat. No. 5,378,619), the light-inducible promoter from the small subunit of ribulose-1,5-bis-phosphate carboxylase (ssRUBISCO), the Adh promoter (Walker et al., *Proc. Natl. Acad. Sci. (U.S.A.)* 84:6624-6628, 1987), the sucrose synthase promoter (Yang et al., *Proc. Natl. Acad. Sci. (U.S.A.)* 87:4144-4148, 1990), the R gene complex promoter (Chandler et al., *The Plant Cell* 1:1175-1183, 1989), the chlorophyll a/b binding protein gene promoter the CsVMV promoter (Verdaguer B et al., 1998); these promoters have been used to create DNA constructs that have been expressed in plants, e.g., PCT publication WO 84/02913. Exemplary tissue-specific promoters include the tomato E4 and E8 promoters (U.S. Pat. No. 5,859,330) and the tomato 2AII gene promoter (Van Haaren M J J et al., 1993).

In one preferred embodiment, HIO128.5 expression is under control of regulatory sequences from genes whose expression is associated with early seed and/or embryo development. Indeed, in a preferred embodiment, the promoter used is a seed-enhanced promoter. Examples of such promoters include the 5' regulatory regions from such genes as napin (Kridl et al., *Seed Sci. Res.* 1:209:219, 1991), globulin (Belanger and Kriz, *Genet.*, 129: 863-872, 1991, GenBank Accession No. L22295), gamma zein Z 27 (Lopes et al., *Mol Gen Genet.*, 247:603-613, 1995), L3 oleosin promoter (U.S. Pat. No. 6,433,252), phaseolin (Bustos et al., *Plant Cell*, 1(9):839-853, 1989), arcelin5 (US 2003/0046727), a soybean 7S promoter, a 7S α promoter (US 2003/0093828), the soybean 7Sα' beta conglycinin promoter, a 7S α' promoter (Beachy et al., *EMBO J.*, 4:3047, 1985; Schuler et al., *Nucleic Acid Res.*, 10(24):8225-8244, 1982), soybean trypsin inhibitor (Riggs et al., *Plant Cell* 1(6):609-621, 1989), ACP (Baerson et al., *Plant Mol. Biol.,* 22(2):255-267, 1993), stearoyl-ACP desaturase (Slocombe et al., *Plant Physiol.* 104(4):167-176, 1994), soybean a' subunit of β-conglycinin (Chen et al., *Proc. Natl. Acad. Sci.* 83:8560-8564, 1986), *Vicia faba* USP (P-Vf.Usp, SEQ ID NO: 1, 2, and 3 in (US 2003/229918) and *Zea mays* L3 oleosin promoter (Hong et al., *Plant Mol. Biol.,* 34(3):549-555, 1997). Also included are the zeins, which are a group of storage proteins found in corn endosperm. Genomic clones for zein genes have been isolated (Pedersen et al., *Cell* 29:1015-1026, 1982; and Russell et al., *Transgenic Res.* 6(2):157-168) and the promoters from these clones, including the 15 kD, 16 kD, 19 kD, 22 kD, 27 kD and genes, could also be used. Other promoters known to function, for example, in corn include the promoters for the following genes: waxy, *Brittle, Shrunken* 2, Branching enzymes I and II, starch synthases, debranching enzymes, oleosins, glutelins and sucrose synthases. Legume genes whose promoters are associated with early seed and embryo development include *V. faba* legumin (Baumlein et al., 1991, Mol Gen Genet. 225:121-8; Baumlein et al., 1992, Plant J 2:233-9), *V. faba* usp (Fiedler et al., 1993, Plant Mol Biol 22:669-79), pea convicilin (Bown et al., 1988, Biochem J 251:717-26), pea lectin (depater et al., 1993, *Plant Cell* 5:877-86), *P. vulgaris* beta phaseolin (Bustos et al., 1991, EMBO J. 10:1469-79), *P. vulgaris* DLEC2 and PHS [beta] (Bobb et al, 1997, Nucleic Acids Res 25:641-7), and soybean beta-Conglycinin, 7S storage protein (Chamberland et al., 1992, Plant Mol Biol 19:937-49).

Cereal genes whose promoters are associated with early seed and embryo development include rice glutelin ("GluA-3," Yoshihara and Takaiwa, 1996, Plant Cell Physiol 37:124-11; "GluB-1," Takaiwa et al., 1996, Plant Mol Biol 30:1207-21; Washida et al., 1999, Plant Mol Biol 40:1-12; "Gt3," Leisy et al., 1990, Plant Mol Biol 14:41-50), rice prolamin (Zhou & Fan, 1993, Transgenic Res 2:141-6), wheat prolamin (Hammond-Kosack et al., 1993, EMBO J. 12:545-54), maize zein (Z4, Matzke et al., 1990, Plant Mol Biol 14:323-32), and barley B-hordeins (Entwistle et al., 1991, Plant Mol Biol 17:1217-31).

Other genes whose promoters are associated with early seed and embryo development include oil palm GLO7A (7S globulin, Morcillo et al., 2001, Physiol Plant 112:233-243), *Brassica napus napin,* 2S storage protein, and napA gene (Josefsson et al., 1987, J Biol Chem 262:12196-201; Stalberg et al., 1993, Plant Mol Biol 1993 23:671-83; Ellerstrom et al., 1996, Plant Mol Biol 32:1019-27), *Brassica napus oleosin* (Keddie et al., 1994, Plant Mol Biol 24:327-40), *Arabidopsis oleosin* (Plant et al., 1994, Plant Mol Biol 25:193-205), *Arabidopsis* FAE1 (Rossak et al., 2001, Plant Mol Biol 46:717-25), *Canavalia gladiata* con A (Yamamoto et al., 1995, Plant Mol Biol 27:729-41), and *Catharanthus roseus* strictosidine synthase (Str, Ouwerkerk and Memelink, 1999, Mol Gen Genet 261:635-43). In another preferred embodiment, regulatory sequences from genes expressed during oil biosynthesis are used (see, e.g., U.S. Pat. No. 5,952,544). Alternative promoters are from plant storage protein genes (Bevan et al, 1993, Philos Trans R Soc Lond B Biol Sci 342:209-15). Additional promoters that may be utilized are described, for example, in U.S. Pat. Nos. 5,378,619; 5,391,725; 5,428,147; 5,447,858; 5,608,144; 5,608,144; 5,614,399; 5,633,441; 5,633,435; and 4,633,436.

In yet another aspect, in some cases it may be desirable to inhibit the expression of endogenous HIO128.5 in a host cell. Exemplary methods for practicing this aspect of the invention include, but are not limited to antisense suppression (Smith, et al., 1988; van der Krol et al., 1988); co-suppression (Napoli, et al., 1990); ribozymes (PCT Publication WO 97/10328); and combinations of sense and antisense (Waterhouse, et al., 1998). Methods for the suppression of endogenous sequences in a host cell typically employ the transcription or transcription and translation of at least a portion of the sequence to be suppressed. Such sequences may be homologous to coding as well as non-coding regions of the endogenous sequence. Antisense inhibition may use the entire cDNA sequence (Sheehy et al., 1988), a partial cDNA sequence including fragments of 5' coding sequence, (Cannon et al., 1990), or 3' non-coding sequences (Ch'ng et al., 1989). Cosuppression techniques may use the entire cDNA sequence (Napoli et al., 1990; van der Krol et al., 1990), or a partial cDNA sequence (Smith et al., 1990).

Standard molecular and genetic tests may be performed to further analyze the association between a gene and an observed phenotype. Exemplary techniques are described below.

1. DNA/RNA Analysis

The stage- and tissue-specific gene expression patterns in mutant versus wild-type lines may be determined, for instance, by in situ hybridization. Analysis of the methylation status of the gene, especially flanking regulatory regions, may be performed. Other suitable techniques include overexpression, ectopic expression, expression in other plant species and gene knock-out (reverse genetics, targeted knock-out, viral induced gene silencing [VIGS, see Baulcombe D, 1999]).

In a preferred application expression profiling, generally by microarray analysis, is used to simultaneously measure differences or induced changes in the expression of many different genes. Techniques for microarray analysis are well known in the art (Schena M et al., Science (1995) 270:467-470; Baldwin D et al., 1999; Dangond F, Physiol Genomics (2000) 2:53-58; van Hal N L et al., J Biotechnol (2000) 78:271-280; Richmond T and Somerville S, Curr Opin Plant Biol (2000) 3:108-116). Expression profiling of individual tagged lines may be performed. Such analysis can identify other genes that are coordinately regulated as a consequence of the overexpression of the gene of interest, which may help to place an unknown gene in a particular pathway.

2. Gene Product Analysis

Analysis of gene products may include recombinant protein expression, antisera production, immunolocalization, biochemical assays for catalytic or other activity, analysis of phosphorylation status, and analysis of interaction with other proteins via yeast two-hybrid assays.

3. Pathway Analysis

Pathway analysis may include placing a gene or gene product within a particular biochemical, metabolic or signaling pathway based on its mis-expression phenotype or by sequence homology with related genes. Alternatively, analysis may comprise genetic crosses with wild-type lines and other mutant lines (creating double mutants) to order the gene in a pathway, or determining the effect of a mutation on expression of downstream "reporter" genes in a pathway.

Generation of Mutated Plants with a HIO128.5 Phenotype

The invention further provides a method of identifying plants that have mutations in, or an allele of, endogenous HIO128.5 that confer a HIO128.5 phenotype, and generating progeny of these plants that also have the HIO128.5 phenotype and are not genetically modified. In one method, called "TILLING" (for targeting induced local lesions in genomes), mutations are induced in the seed of a plant of interest, for example, using EMS treatment. The resulting plants are grown and self-fertilized, and the progeny are used to prepare DNA samples. HIO128.5-specific PCR is used to identify whether a mutated plant has a HIO128.5 mutation. Plants having HIO128.5 mutations may then be tested for the HIO128.5 phenotype, or alternatively, plants may be tested for the HIO128.5 phenotype, and then HIO128.5-specific PCR is used to determine whether a plant having the HIO128.5 phenotype has a mutated HIO128.5 gene. TILLING can identify mutations that may alter the expression of specific genes or the activity of proteins encoded by these genes (see Colbert et al. (2001) Plant Physiol 126:480-484; McCallumn et al. (2000) Nature Biotechnology 18:455-457).

In another method, a candidate gene/Quantitative Trait Locus (QTLs) approach can be used in a marker-assisted breeding program to identify alleles of or mutations in the HIO128.5 gene or orthologs of HIO128.5 that may confer the HIO128.5 phenotype (see Foolad et al., Theor Appl Genet. (2002) 104(6-7):945-958; Rothan et al., Theor Appl Genet (2002) 105(1):145-159; Dekkers and Hospital, Nat Rev Genet. (2002) January; 3(1):22-32).

Thus, in a further aspect of the invention, a HIO128.5 nucleic acid is used to identify whether a plant having a HIO128.5 phenotype has a mutation in endogenous HIO128.5 or has a particular allele that causes the HIO128.5 phenotype compared to plants lacking the mutation or allele, and generating progeny of the identified plant that have inherited the HIO128.5 mutation or allele and have the HIO128.5 phenotype.

While the invention has been described with reference to specific methods and embodiments, it will be appreciated that various modifications and changes may be made without departing from the invention. All publications cited herein are expressly incorporated herein by reference for the purpose of describing and disclosing compositions and methodologies that might be used in connection with the invention. All cited patents, patent applications, and sequence information in referenced public databases are also incorporated by reference.

EXAMPLES

Example 1

Generation of Plants with a HIO128.5 Phenotype by Transformation with an Activation Tagging Construct Mutants were generated using the activation tagging "ACT-TAG" vector, pSKI015 (GI#6537289; Weigel D et al., 2000). Standard methods were used for the generation of *Arabidopsis* transgenic plants, and were essentially as described in published application PCT WO0183697. Briefly, T0 *Arabidopsis* (Col-0) plants were transformed with *Agrobacterium* carrying the pSKI015 vector, which comprises T-DNA derived from the *Agrobacterium* Ti plasmid, an herbicide resistance selectable marker gene, and the 4× CaMV 35S enhancer element. Transgenic plants were selected at the T1 generation based on herbicide resistance.

T3 seed pools were analyzed by Near Infrared Spectroscopy (NIR) intact at time of harvest. NIR infrared spectra were captured using a Brulcer 22 N/F near infrared spectrometer. Bruker Software was used to estimate total seed oil and total seed protein content using data from NIR analysis and reference methods according to the manufacturers instructions. Oil content predicting calibrations were developed following the general method of AOCS Procedure Am 1-92, Official Methods and Recommended Practices of the American Oil Chemists Society, 5$^{th}$ Ed., AOCS, Champaign Ill.). Calibrations allowing NIR predictions of Crude Oil (Ether Extract) (PDXOil3, AOAC Method 920.39 (Fat(Crude) or Ether Extract in Animal Feed, AOAC International, Official Methods of Analysis, 17th Edition, AOAC International, Gaithersburg Md.) and Crude Oil ASE (Ren Oil, Accelerated Solvent Extraction) NIR predicted oil contents were determined for over 81,307 individual ACTTAG lines. To identify high oil lines the NIR oil result was compared to the mean oil result for all ACTTAG lines planted in the same flat (Relative oil content). Oil Content distance (SD_Distance) was determined by taking the NIR predicted oil content of the individual, subtracting the mean oil content for the flat from which the individual came, then dividing the result by the flat standard deviation. This creates a real number measure of distance, in standard deviations, that each samples result lies from the flat average. From 81,307 oil determinations high oil results were selected by eliminating all lines with an ASE predicted oil content SD_DISTANCE of <2. ACTTAG lines that had ASE oil predictions with an SD_Distance>=2 were compared to identify lines sharing a flanking sequence tag placement location that occurred in the same 10 kb region in two distinct lines. The genome coordinates in this subset of high oil ACTTAG lines was evaluated and lines having two or more independent ACTTAG insertions, also displaying high oil, were identified and the flanking sequence confirmed by PCR and sequencing.

Line W000041352 (IN009897) had a NIR determined oil content of 39.2% relative to a flat average oil content of 35.2% (111% of Flat Average). Line W000210144 (IN088075) had a NIR determined oil content of 30.2% relative to a flat average oil content of 24.2% (124% of Flat Average).

Line W000041352 (IN009897) had a confirmed ACTTAG insertion on Chromosome 5 at bp 15023687. Line W000210144 (IN088075) had a confirmed ACTTAG insertion on Chromosome 5 at bp 15020099.

Example 2

Characterization of the T-DNA Insertion in Plants Exhibiting the Altered Oil Content Phenotype We performed standard molecular analyses, essentially as described in patent application PCT WO0183697, to determine the site of the T-DNA insertion associated with the altered oil content phenotype. Briefly, genomic DNA was extracted from plants exhibiting the altered oil content phenotype. PCR, using primers specific to the pSKI015 vector, confirmed the presence of the 35S enhancer in plants from lines IN009897 and IN088075, and Southern blot analysis verified the genomic integration of the ACTTAG T-DNA and showed the presence of the T-DNA insertions in each of the transgenic lines.

Inverse PCR was used to recover genomic DNA flanking the T-DNA insertion, which was then subjected to sequence analysis using a basic BLASTN search and/or a search of the publicly available *Arabidopsis* Information Resource (TAIR) database. For ACTTAG line IN009897, there was sequence identity to nucleotides 31217-8456 on *Arabidopsis* BAC clone K22F20 on chromosome 5 (GI#3449314), placing the left border junction upstream from nucleotide 8456 (GI#3449314). Left border of IN009897 T-DNA was about 340 bp 5' of the translation start site.

For ACTTAG line IN088075, there was sequence identity to nucleotides 4490-4828 on *Arabidopsis* BAC clone K22F20 on chromosome 5 (GI#3449314), placing the left border junction upstream from nucleotide 4828 (GI#3449314). Left border IN088075 T-DNA was about 3248 bp 5' of the translation start site.

Example 3

Analysis of *Arabidopsis* HIO128.5 Sequence

Sequence analyses were performed with BLAST (Altschul et al., 1990, J. Mol. Biol. 215:403-410), PFAM (Bateman et al., 1999, Nucleic Acids Res 27:260-262), PSORT (Nakai K, and Horton P, 1999, Trends Biochem Sci 24:34-6), and/or CLUSTAYL (Thompson J D et al., 1994, Nucleic Acids Res 22:4673-4680).

TBLASTN Against est_Others Results:

The candidate gene At5g37780 is supported by the NCBI entry GI#30693152. There are many ESTs from diverse plant species showing similarity to At5g37780. If possible, ESTs contigs of each species were made. The top hit for each of the following species are listed below and included in the "Orthologue Table" (Table 1): *Triticum aestivum, Gossypium hirsutum, Zea mays, Glycine max, Mentha x piperita, Populus tremula, Oryza sativa, Lycopersicon esculentumi, Solanum tuberosumi*, and *Beta vulgaris*.

1. One EST Contig from Wheat

The contigged sequence is presented as SEQ ID NO: 3.

2. One EST Contig from Cotton

The contigged sequence is presented as SEQ ID NO: 4.

3. One EST Contig from Maize

The contigged sequence is presented as SEQ ID NO: 5.

4. One EST Contig from Soybean

The contigged sequence is presented as SEQ ID NO: 6.

5. One EST from Mint gi|7244443 AW255191 ML181 peppermint glandular trichome *Menthaxpiperita* cDNA, mRNA sequence.

6. One EST Contig from Poplars

The contigged sequence is presented as SEQ ID NO: 7.

7. One EST Contig from Rice

The contigged sequence is presented as SEQ ID NO: 8.

8. One EST Contig from Tomato

The contigged sequence is presented as SEQ ID NO: 9.

9. One EST Contig from Potato

The contigged sequence is presented as SEQ ID NO: 10.

10. One EST Contig from Sugar Beet

The contigged sequence is presented as SEQ ID NO: 11.

BLASTP Against a Protein Database Based on a Translation of the *Arabidopsis* genome sequences from the *Arabidopsis* Genome Initiative (ATH1_aa):

The protein At5g37780 has homology to large numbers of EF-hand-containing proteins from plants, fungi and animals. The *Arabidopsis* genome encodes more than 200 such proteins. In order to identify genes that are most likely to carryout similar function as At5g37780 (calmodulin 1, CaM1), the top 6 BLAST results and the BLAST results for At2g41090, At3g22930, At4 g14640 are listed below. This is because these genes form a subclade among the EF-hand-containing proteins in *Arabidopsis*.

1. At5g37780 Itself

>gi|15240343|ref|NP_198594.11 calmodulin 4 [*Arabidopsis thaliana*]

Score=760 (272.6 bits), Expect 1.7e−76, P=1.7e−76

2. At1g66410 from *Arabidopsis*

>gi|152196521 calmodulin 1

Score=760 (272.6 bits), Expect=1.7e−76, P=1.7e−76

3. At3g43810 from *Arabidopsis* gi|15229784 calmodulin 7

Score=750 (269.1 bits), Expect=1.9e−75, P=1.9e−75

4. At2g27030 from *Arabidopsis* gi|30683369 calmodulin 5

Score=747 (268.0 bits), Expect=4.0e−75, P=4.0e−75

The following sequences are other splice variants of At2g27030.

gi|30683366 gi|15225840

5. At2g41110 from *Arabidopsis* gi|30688531 calmodulin 2

Score=747 (268.0 bits), Expect=4.0e−75, P=4.0e−75

6. At3g56800 from *Arabidopsis* gi|5229010 calmodulin 3

Score=747 (268.0 bits), Expect=4.0e−75, P=4.0e−75

7. At3g22930 from *Arabidopsis* gi|15228905

Score=599 (215.9 bits), Expect=1.9e−59, P=1.9e−59

8. At4g14640 from *Arabidopsis* gi|15233513 calmodulin 8

Score=586 (211.3 bits), Expect=4.6e−58, P=4.6e−58

9. At2g41090 from *Arabidopsis* gi|15226831 calcium binding protein-22

Score=470 (170.5 bits), Expect=9.0e−46, P=9.0e−46

TABLE 1

| Ortholog Gene Name | Species | GI # | % ID to HIO128.5 | Score(s) (BLAST, Clustal, etc.) |
|---|---|---|---|---|
| One EST contig from | *Triticum aestivum* | GI: 9423020<br>GI: 9696144 | Length = 846<br>Identities = 145/149 (97%), | TBLASTN<br>Score = 750 (269.1 bits), |

TABLE 1-continued

| Ortholog Gene Name | Species | GI # | % ID to HIO128.5 | Score(s) (BLAST, Clustal, etc.) |
|---|---|---|---|---|
| wheat | | GI: 13634666<br>GI: 17147124<br>GI: 17144651<br>GI: 20441856<br>GI: 21831548<br>GI: 21828973<br>GI: 21841613 | Positives = 149/149 (100%),<br>Frame = +1 | Expect = 3.1e−74, P = 3.1e−74 |
| One EST contig from cotton | *Gossypium hirsutum* | GI: 5049985<br>GI: 5046037<br>GI: 5049489<br>GI: 5049563<br>GI: 5050006<br>GI: 31073123 | Length = 825<br>Identities = 124/129 (96%),<br>Positives = 128/129 (99%),<br>Frame = +1 | TBLASTN<br>Score = 639 (230.0 bits),<br>Expect = 1.6e−71, Sum<br>P(2) = 1.6e−71 |
| One EST contig from maize | *Zea mays* | gi|4646456<br>gi|19821984<br>gi|19769811 | Length = 764<br>Identities = 145/149 (97%),<br>Positives = 149/149 (100%),<br>Frame = −3 | TBLASTN<br>Score = 750 (269.1 bits),<br>Expect = 1.3e−74, P = 1.3e−74 |
| One EST contig from soybean | *Glycine max* | GI: 4313432<br>GI: 5606550<br>GI: 6200939<br>GI: 6073041<br>GI: 6134135<br>GI: 6134485<br>GI: 6227734<br>GI: 6095150<br>GI: 6666558<br>GI: 6847152<br>GI: 7030091<br>GI: 7147350<br>GI: 7796245<br>GI: 7639685<br>GI: 15285510<br>GI: 15662151<br>GI: 15812578<br>GI: 21676062<br>GI: 20811746<br>GI: 21677386<br>GI: 22524651<br>GI: 23726465<br>GI: 26056780 | Length = 1009<br>Identities = 146/149 (97%),<br>Positives = 149/149 (100%),<br>Frame = +2 | TBLASTN<br>Score = 753 (270.1 bits),<br>Expect = 7.9e−75, P = 7.9e−75 |
| One EST from mint | *Mentha x piperita* | gi|7244443 | Length = 630<br>Identities = 139/141 (98%),<br>Positives = 141/141 (100%),<br>Frame = +3 | TBLASTN<br>Score = 716 (257.1 bits),<br>Expect = 2.1e−72, P = 2.1e−72 |
| One EST contig from poplars | *Populus tremula* | GI: 3854505<br>GI: 3855499<br>GI: 23962741<br>GI: 24016450<br>GI: 24008628<br>GI: 24003649<br>GI: 24012511<br>GI: 24019849 | Length = 856<br>Identities = 145/149 (97%),<br>Positives = 149/149 (100%),<br>Frame = +2 | TBLASTN<br>Score = 750 (269.1 bits),<br>Expect = 8.1e−75, P = 8.1e−75 |
| One EST contig from rice | *Oryza sativa* | GI: 15848158<br>GI: 15855278<br>GI: 15851729<br>GI: 15848322<br>GI: 15851219<br>GI: 15851316<br>GI: 15853653<br>GI: 15856122<br>GI: 15856922<br>GI: 474015<br>GI: 218139<br>GI: 2809480<br>GI: 3107875<br>GI: 9788913<br>GI: 14981797<br>GI: 28298188 | Length = 854<br>Identities = 146/149 (97%),<br>Positives = 149/149 (100%),<br>Frame = +1 | TBLASTN<br>Score = 753 (270.1 bits),<br>Expect = 4.0e−75, P = 4.0e−75 |
| One EST contig from tomato | *Lycopersicon esculentum* | gi|12628539<br>gi|5274456 | Length = 1116<br>Identities = 144/149 (96%),<br>Positives = 149/149 (100%),<br>Frame = +2 | TBLASTN<br>Score = 747 (268.0 bits),<br>Expect = 2.4e−74, P = 2.4e−74 |
| One EST contig from potato | *Solanum tuberosum* | GI: 10448778<br>GI: 10808121<br>GI: 12586187<br>GI: 13608457 | Length = 863<br>Identities = 145/149 (97%),<br>Positives = 149/149 (100%),<br>Frame = +3 | TBLASTN<br>Score = 750 (269.1 bits),<br>Expect = 8.9e−75, P = 8.9e−75 |

TABLE 1-continued

| Ortholog Gene Name | Species | GI # | % ID to HIO128.5 | Score(s) (BLAST, Clustal, etc.) |
|---|---|---|---|---|
| | | GI: 13608600 | | |
| | | GI: 15256182 | | |
| | | GI: 14642206 | | |
| | | GI: 15259712 | | |
| | | GI: 20164940 | | |
| | | GI: 20167361 | | |
| | | GI: 20167360 | | |
| | | GI: 20167361 | | |
| | | GI: 20167360 | | |
| | | GI: 21915724 | | |
| | | GI: 21916942 | | |
| One EST contig from sugar beet | Beta vulgaris | GI: 15428011 GI: 21334791 GI: 15428007 GI: 14522451 GI: 15427869 GI: 21333374 GI: 21334749 GI: 21334893 GI: 21334760 GI: 26112606 GI: 7789900 GI: 21334240 GI: 21334749 | Length = 878 Identities = 144/149 (96%), Positives = 149/149 (100%), Frame = +1 | TBLASTN Score = 746 (267.7 bits), Expect = 8.7e−75, P = 8.7e−75 |

TABLE 2

Closest *Arabidopsis* homologs:

| At1g66410 | Arabidopsis thaliana | >gi|15219652| | Length = 150 Identities = 149/149 (100%), Positives = 149/149 (100%) | BLASTP Score = 760 (272.6 bits), Expect = 1.7e−76, P = 1.7e−76 |
|---|---|---|---|---|
| At3g43810 | Arabidopsis thaliana | gi|15229784 | Length = 150 Identities = 145/149 (97%), Positives = 149/149 (100%) | BLASTP Score = 750 (269.1 bits), Expect = 1.9e−75, P = 1.9e−75 |
| At2g27030 | Arabidopsis thaliana | gi|30683369 | Length = 182 Identities = 144/149 (96%), Positives = 149/149 (100%) | BLASTP Score = 747 (268.0 bits), Expect = 4.0e−75, P = 4.0e−75 |
| At2g41110 | Arabidopsis thaliana | gi|30688531 | Length = 150 Identities = 144/149 (96%), Positives = 149/149 (100%) | BLASTP Score = 747 (268.0 bits), Expect = 4.0e−75, P = 4.0e−75 |
| At3g56800 | Arabidopsis thaliana | gi|15229010 | Length = 150 Identities = 144/149 (96%), Positives = 149/149 (100%) | BLASTP Score = 747 (268.0 bits), Expect = 4.0e−75, P = 4.0e−75 |
| At3g22930 | Arabidopsis thaliana | gi|15228905 | Length = 174 Identities = 110/144 (76%), Positives = 132/144 (91%) | BLASTP Score = 599 (215.9 bits), Expect = 1.9e−59, P = 1.9e−59 |
| At4g14640 | Arabidopsis thaliana | gi|15233513 | Length = 152 Identities = 108/143 (75%), Positives = 131/143 (91%) | BLASTP Score = 586 (211.3 bits), Expect = 4.6e−58, P = 4.6e−58 |
| At2g41090 | Arabidopsis thaliana | gi|15226831 | Length = 192 Identities = 95/149 (63%), Positives = 121/149 (81%) | BLASTP Score = 470 (170.5 bits), Expect = 9.0e−46, P = 9.0e−46 |

At5g37780 is a non-secretory protein that lacks transmembrane domain (predicted by TMHMM (Krogh et al, J. Mol. Biol. 2001 305:567-580)) and signal peptide (predicted by SignalP). At5g37780 is likely to be a cytoplasmic protein based on Psort2 analysis (26% nuclear, 44% cytoplasmic, 20% mitochondrial, 8% cytoskeletal by Psort2).

Pfam analysis showed that At5g37780 has four EF-hand domains (PF00036, SM00054). Many Ca2+-binding proteins belong to the same evolutionary family and share a type of Ca2+-binding domain known as the EF-hand. This type of domain consists of a twelve-residue loop flanked on both sides by a twelve-residue-helical domain. In an EF-hand loop the Ca2+ ion is coordinated in a pentagonal bipyramidal configuration. The six residues involved in the binding are in positions 1, 3, 5, 7, 9 and 12; these residues are denoted by X, Y, Z, −Y, −X and −Z. The invariant Glu or Asp at position 12 provides two oxygens for liganding Ca (bidentate ligand).

Ca2+ is an important messenger mediating plant responses to hormones, developmental cues and external stimuli. Changes in intracellular concentration of Ca2+ is implicated in regulating diverse cellular process such as cytoplasmic streaming, thigmotropism, gravitropism, cell division, cell elongation, cell differentiation, cell polarity, photomorphogenesis and plant defense and stress responses. Transient increase in the concentration of Ca2+ in the cytoplasm is sensed by Ca2+ binding proteins. The conformation of these protein changes when they bind Ca2+, resulting in modulation of its activity or its ability to interact with other proteins or nucleic acids and modulate their function or activity. One such class of proteins is calmodulin, which contains EF-hand motifs.

At5g37780 (calmodulin 1) is one of nine calmodulins reported in the literature. The amino acid sequences of these proteins are highly conserved. These proteins, together with a few other proteins, form a subdlade withing the class IV family of EF-hand containing proteins. The blastP alignments between At5g37780 and these proteins were described above, except AtCaM6. This is because AtCaM6 has not been given a protein identification number. Calmodulins are highly conserved small molecular weight acidic proteins that have 4 EF-hands and bind four molecules of Ca2+. Binding of Ca2+ to calmodulin results in conformational change which then allows calmodulin to interact with target proteins (e.g. calmodulin binding proteins) to modulate their activity or function.

In this context, it seems likely that At5g37780 is involved in signal transduction in *Arabidopsis*.

| Model | Domain | seq-f* | seq-t | hmm-f | hmm-t | score | E-value |
|---|---|---|---|---|---|---|---|
| PFO0036 | 1/4 | 12 | 40 .. | 1 | 29 [ ] | 41.0 | 3.8e−09 |
| PFO0036 | 1/4 | 12 | 40 .. | 1 | 29 [ ] | 41.0 | 5.5e−09 |
| SMO0054 | 1/4 | 12 | 40 .. | 1 | 29 [ ] | 42.2 | 1.6e−09 |
| SMO0054 | 1/4 | 12 | 40 .. | 1 | 29 [ ] | 42.2 | 2.5e−09 |
| PFO0036 | 2/4 | 48 | 76 .. | 1 | 29 [ ] | 39.4 | 1.7e−08 |
| SMO0054 | 2/4 | 48 | 76 .. | 1 | 29 [ ] | 44.1 | 4.2e−10 |
| SMO0054 | 2/4 | 48 | 76 .. | 1 | 29 [ ] | 44.1 | 6.4e−10 |
| SMO0054 | 3/4 | 85 | 113 .. | 1 | 29 [ ] | 43.4 | 7.2e−10 |
| SMO0054 | 3/4 | 85 | 113 .. | 1 | 29 [ ] | 43.4 | 1.1e−09 |
| PFO0036 | 3/4 | 85 | 113 .. | 1 | 29 [ ] | 42.2 | 1.6e−09 |
| PFO0036 | 3/4 | 85 | 113 .. | 1 | 29 [ ] | 42.1 | 2.6e−09 |
| PFO0036 | 4/4 | 121 | 149 .] | 1 | 29 [ ] | 43.1 | 8.6e−10 |
| PFO0036 | 4/4 | 121 | 149 .] | 1 | 29 [ ] | 43.1 | 1.3e−09 |
| SMO0054 | 4/4 | 121 | 149 .] | 1 | 29 [ ] | 46.3 | 9.4e−11 |
| SMO0054 | 4/4 | 121 | 149 .] | 1 | 29 [ ] | 46.3 | 1.4e−10 |

*seq-f refers to "sequence-from" and seq-t refers to "sequence-to." The two periods following the seq-t number indicate that the matching region was within the sequence and did not extend to either end. The period followed by the right bracket indicate that the matching region extends to the end of the sequence. The two brackets indicate that the match spanned the entire length of the profile HMM. hmm-f and hmm-t refer to the beginning and ending coordinates of the matching portion of the profile HMM.

Example 4

Recapitulation of the High Oil Phenotype

To test whether over-expression of At5g37780 causes high seed oil phenotype, oil content in seeds from transgenic plants over-expressing this gene was compared with oil content in seeds from non-transgenic control plants. To do this, *Arabidopsis* plants of the Col-0 ecotype were transformed by *Agrobacterium* mediated transformation using the floral dip method, with a construct containing the coding sequences of the HIO128.5 gene (At5g37780) behind the CsVMV promoter and in front of the nos terminator or a control gene unrelated to pathogen resistance. Both of these constructs contain the nptII gene driven by the RE4 promoter to confer kanamycin resistance in plants and serve as healthy green plants. T1 seed was harvested from the transformed plants and transformants selected by germinating seed on agar medium containing kanamycin. Kanamycin resistant transformants were transplanted to soil after 7 days. Control plants were germinated on agar medium without kanamycin, transplanted to soil after 7 days. Twenty-two plants containing the CsVMV:: HIO128.5 transgene along with 10 Col-0 control plants were grown in the same flat in the growth room. All plants were allowed to self-fertilize and set seed.

To evaluate the high seed oil phenotype T2 seed pools were analyzed by Near Infrared Spectroscopy (NIR) at time of harvest. NIR infrared spectra were captured using a Bruker 22 N/F near infrared spectrometer. Bruker Software was used to estimate total seed oil and total seed protein content using data from NIR analysis and reference methods according to the manufacturers instructions. Oil contents predicted by our calibration (ren oil 1473 1d+sline.q2, Predicts Hexane Extracted Oil), followed the general method of AOCS Procedure AM1-92, Official Methods and Recommended Practices of the American Oil Chemists Society, 5th Ed., AOCS, Champaign, Ill. Seed from transgenic plants and control plants grown in the same flat were compared and the results are presented in Table 3.

To compare the effect of over-expression of HIO128.5 on seed oil accumulation, four experiments were performed. In three of four experiments, plants over-expressing the At5g37780 had higher seed oil content than the control plants grown in the same flat. Across experiments, the average seed oil content of plants over-expressing HIO128.5 was 3.2% greater than the untransformed controls; the seed oil content in plants over-expressing HIO128.5 was significantly greater than non-transgenic control plants (two-way ANOVA (analysis of variance); P=0.11).

TABLE 3

| Experiment | Plant ID | Transgene | Predicted average | Relative value average |
|---|---|---|---|---|
| 1 | DX04475001 | CsVMV::At5g37770 | 34.10 | 104.39 |
| 1 | DX04475004 | CsVMV::At5g37770 | 34.25 | 104.86 |
| 1 | DX04475005 | CsVMV::At5g37770 | 35.50 | 108.68 |
| 1 | DX04475006 | CsVMV::At5g37770 | 30.37 | 92.98 |
| 1 | DX04475007 | CsVMV::At5g37770 | 32.84 | 100.54 |
| 1 | DX04475008 | CsVMV::At5g37770 | 36.10 | 110.51 |
| 1 | DX04475009 | CsVMV::At5g37770 | 36.38 | 111.37 |
| 1 | DX04475010 | CsVMV::At5g37770 | 36.61 | 112.08 |
| 1 | DX04475011 | CsVMV::At5g37770 | 34.97 | 107.05 |
| 1 | DX04475012 | CsVMV::At5g37770 | 32.15 | 98.43 |
| 1 | DX04475013 | CsVMV::At5g37770 | 33.76 | 103.35 |
| 1 | DX04475014 | CsVMV::At5g37770 | 35.74 | 109.41 |
| 1 | DX04475015 | CsVMV::At5g37770 | 33.45 | 102.39 |
| 1 | DX04475016 | CsVMV::At5g37770 | 34.69 | 106.19 |
| 1 | DX04475017 | CsVMV::At5g37770 | 34.27 | 104.90 |
| 1 | DX04475018 | CsVMV::At5g37770 | 34.25 | 104.86 |
| 1 | DX04475019 | CsVMV::At5g37770 | 34.48 | 105.56 |
| 1 | DX04475020 | CsVMV::At5g37770 | 32.08 | 98.22 |
| 1 | DX04475021 | CsVMV::At5g37770 | 33.00 | 101.03 |
| 1 | DX04475022 | CsVMV::At5g37770 | 34.49 | 105.59 |
| 1 | DX04492001 | None | 34.05 | 104.24 |
| 1 | DX04492002 | None | 33.22 | 101.69 |
| 1 | DX04492003 | None | 29.35 | 89.85 |
| 1 | DX04492004 | None | 33.59 | 102.83 |
| 1 | DX04492005 | None | 33.85 | 103.62 |
| 1 | DX04492006 | None | 36.69 | 112.33 |
| 1 | DX04492007 | None | 33.43 | 102.34 |
| 1 | DX04492008 | None | 32.03 | 98.05 |
| 1 | DX04492009 | None | 31.10 | 95.21 |
| 1 | DX04492010 | None | 29.35 | 89.84 |
| 2 | DX06816001 | CsVMV::At5g37770 | 25.99 | 96.27 |
| 2 | DX06816002 | CsVMV::At5g37770 | 28.87 | 106.93 |
| 2 | DX06816003 | CsVMV::At5g37770 | 27.04 | 100.14 |
| 2 | DX06816004 | CSVMV::At5g37770 | 25.99 | 96.26 |
| 2 | DX06816005 | CsVMV::At5g37770 | 28.68 | 106.22 |
| 2 | DX06816006 | CsVMV::At5g37770 | 30.40 | 112.60 |
| 2 | DX06816007 | CsVMV::At5g37770 | 27.57 | 102.11 |
| 2 | DX06816008 | CsVMV::At5g37770 | 26.34 | 97.58 |
| 2 | DX06816009 | CsVMV::At5g37770 | 27.14 | 100.52 |
| 2 | DX06816010 | CsVMV::At5g37770 | 28.14 | 104.25 |
| 2 | DX06816011 | CsVMV::At5g37770 | 27.70 | 102.60 |
| 2 | DX06816012 | CsVMV::At5g37770 | 26.14 | 96.82 |

TABLE 3-continued

| Experiment | Plant ID | Transgene | Predicted average | Relative value average |
|---|---|---|---|---|
| 2 | DX06816013 | CsVMV::At5g37770 | 27.43 | 101.61 |
| 2 | DX06816014 | CsVMV::At5g37770 | 28.34 | 104.98 |
| 2 | DX06816015 | CsVMV::At5g37770 | 27.34 | 101.26 |
| 2 | DX06816016 | CsVMV::At5g37770 | 28.40 | 105.19 |
| 2 | DX06816017 | CsVMV::At5g37770 | 30.38 | 112.53 |
| 2 | DX06816018 | CsVMV::At5g37770 | 27.01 | 100.04 |
| 2 | DX06816019 | CsVMV::At5g37770 | 29.69 | 109.97 |
| 2 | DX06816020 | CsVMV::At5g37770 | 27.19 | 100.72 |
| 2 | DX06816021 | CsVMV::At5g37770 | 28.79 | 106.62 |
| 2 | DX06816022 | CsVMV::At5g37770 | 31.37 | 116.20 |
| 2 | DX06798001 | None | 25.00 | 92.61 |
| 2 | DX06798002 | None | 29.91 | 110.77 |
| 2 | DX06798003 | None | 27.04 | 100.14 |
| 2 | DX06798004 | None | 26.34 | 97.58 |
| 2 | DX06798005 | None | 26.96 | 99.85 |
| 2 | DX06798006 | None | 26.27 | 97.29 |
| 2 | DX06798007 | None | 26.64 | 98.66 |
| 2 | DX06798008 | None | 27.87 | 103.25 |
| 2 | DX06798009 | None | 27.10 | 100.36 |
| 2 | DX06798010 | None | 26.86 | 99.49 |
| 3 | DX07579001 | CsVMV::At5g37770 | 32.70 | 106.04 |
| 3 | DX07579002 | CsVMV::At5g37770 | 31.04 | 100.66 |
| 3 | DX07579003 | CsVMV::At5g37770 | 33.55 | 108.79 |
| 3 | DX07579004 | CsVMV::At5g37770 | 32.53 | 105.49 |
| 3 | DX07579005 | CsVMV::At5g37770 | 30.53 | 99.02 |
| 3 | DX07579006 | CsVMV::At5g37770 | 30.89 | 100.18 |
| 3 | DX07579007 | CsVMV::At5g37770 | 30.28 | 98.21 |
| 3 | DX07579008 | CsVMV::At5g37770 | 29.15 | 94.55 |
| 3 | DX07579010 | CsVMV::At5g37770 | 33.35 | 108.16 |
| 3 | DX07597001 | None | 33.22 | 107.74 |
| 3 | DX07597002 | None | 29.65 | 96.16 |
| 3 | DX07597003 | None | 30.45 | 98.74 |
| 3 | DX07597004 | None | 30.41 | 98.62 |
| 3 | DX07597005 | None | 30.55 | 99.07 |
| 3 | DX07597007 | None | 31.57 | 102.39 |
| 3 | DX07597009 | None | 30.05 | 97.45 |
| 3 | DX07597010 | None | 30.78 | 99.82 |
| 4 | DX07623001 | CsVMV::At5g37770 | 30.19 | 97.47 |
| 4 | DX07623002 | CsVMV::At5g37770 | 33.51 | 108.19 |
| 4 | DX07623003 | CsVMV::At5g37770 | 37.62 | 121.45 |
| 4 | DX07623004 | CsVMV::At5g37770 | 32.26 | 104.13 |
| 4 | DX07623005 | CsVMV::At5g37770 | 29.92 | 96.58 |
| 4 | DX07641001 | None | 26.82 | 86.58 |
| 4 | DX07641002 | None | 29.86 | 96.40 |
| 4 | DX07641003 | None | 32.07 | 103.51 |
| 4 | DX07641005 | None | 31.90 | 102.97 |
| 4 | DX07641006 | None | 31.71 | 102.35 |
| 4 | DX07641007 | None | 31.19 | 100.68 |
| 4 | DX07641008 | None | 30.70 | 99.11 |
| 4 | DX07641009 | None | 32.84 | 106.01 |
| 4 | DX07641010 | None | 31.72 | 102.39 |

Example 5

Transformed explants of rapeseed, soy, corn, sunflower, cotton, cocoa, safflower, oil palm, coconut palm, flax, castor and peanut are obtained through *Agrobacterium tumefaciens*-mediated transformation or microparticle bombardment. Plants are regenerated from transformed tissue. The greenhouse grown plants are then analyzed for the gene of interest expression levels as well as oil levels.

Example 6

This example provides analytical procedures to determine oil and protein content, mass differences, amino acid composition, free amino acid levels, and micronutrient content of transgenic maize plants.

Oil levels (on a mass basis and as a percent of tissue weight) of first generation single corn kernels and dissected germ and endosperm are determined by low-resolution $^1$H nuclear magnetic resonance (NMR) (Tiwari et al., *JAOCS*, 51:104-109 (1974); or Rubel, *JAOCS*, 71:1057-1062 (1994)), whereby NMR relaxation times of single kernel samples are measured, and oil levels are calculated based on regression analysis using a standard curve generated from analysis of corn kernels with varying oil levels as determined gravimetrically following accelerated solvent extraction. One-way analysis of variance and the Student's T-test (JMP, version 4.04, SAS Institute Inc., Cary, N.C., USA) are performed to identify significant differences between transgenic and non-transgenic kernels as determined by transgene-specific PCR.

Oil levels and protein levels in second generation seed are determined by NIT spectroscopy, whereby NIT spectra of pooled seed samples harvested from individual plants are measured, and oil and protein levels are calculated based on regression analysis using a standard curve generated from analysis of corn kernels with varying oil or protein levels, as determined gravimetrically following accelerated solvent extraction or elemental (% N) analysis, respectively. One-way analysis of variance and the Student's T-test are performed to identify significant differences in oil (% kernel weight) and protein (% kernel weight) between seed from marker positive and marker negative plants.

The levels of free amino acids are analyzed from each of the transgenic events using the following procedure. Seeds from each of the transgenic plants are crushed individually into a fine powder and approximately 50 mg of the resulting powder is transferred to a pre-weighed centrifuge tube. The exact sample weight is recorded and 1.0 ml of 5% trichloroacetic acid is added to each sample tube. The samples are mixed at room temperature by vortex and then centrifuged for 15 minutes at 14,000 rpm on an Eppendorf microcentrifuge (Model 5415C, Brinkmann Instrument, Westbury, N.Y.). An aliquot of the supernatant is removed and analyzed by HPLC (Agilent 1100) using the procedure set forth in Agilent Technical Publication "Amino Acid Analysis Using the Zorbax Eclipse-AAA Columns and the Agilent 1100 HPLC," Mar. 17, 2000.

Quantitative determination of total amino acids from corn is performed by the following method. Kernels are ground and approximately 60 mg of the resulting meal is acid-hydrolyzed using 6 N HCl under reflux at 100° C. for 24 hrs. Samples are dried and reconstituted in 0.1 N HCl followed by precolumn derivatization with α-phthalaldehyde (OPAO for HPLC analysis. The amino acids are separated by a reverse-phase Zorbax Eclipse XDB-C18 HPLC column on an Agilent 1100 HPLC (Agilent, Palo Alto, Calif.). The amino acids are detected by fluorescence. Cysteine, proline, asparagine, glutamine, and tryptophan are not included in this amino acid screen (Henderson et al, "Rapid, Accurate, Sensitive and Reproducible HPLC Analysis of Amino acids, Amino Acid Analysis Using Zorbax Eclipse-AAA Columns and the Agilent 1100 HPLC," Agilent Publication (2000); see, also, "Measurement of Acid-Stable Amino Acids," AACC Method 07-01 (American Association of Cereal Chemists, Approved Methods, 9th edition (LCCC#95-75308)). Total tryptophan is measured in corn kernels using an alkaline hydrolysis method as described (Approved Methods of the American Association of Cereal Chemists—10$^{th}$ edition, AACC ed, (2000) 07-20 Measurement of Tryptophan—Alakline Hydrolysis).

Tocopherol and tocotrienol levels in seeds are assayed by methods well-known in the art. Briefly, 10 mg of seed tissue are added to 1 g of microbeads (Biospec Product Inc, Barlesville, Okla.) in a sterile microfuge tube to which 500 µl 1% pyrogallol (Sigma Chemical Co., St. Louis, Mo.)/ethanol have been added. The mixture is shaken for 3 minutes in a mini Beadbeater (Biospec) on "fast" speed, then filtered through a 0.2 µm filter into an autosampler tube. The filtered extracts are analyzed by HPLC using a Zorbax silica HPLC column (4.6 mm×250 mm) with a fluorescent detection, an excitation at 290 nm, an emission at 336 nm, and bandpass and slits. Solvent composition and running conditions are as listed below with solvent A as hexane and solvent B as methyl-t-butyl ether. The injection volume is 20 µl, the flow rate is 1.5 ml/minute and the run time is 12 minutes at 40° C. The solvent gradient is 90% solvent A, 10% solvent B for 10 minutes; 25% solvent A, 75% solvent B for 11 minutes; and 90% solvent A, 10% solvent B for 12 minutes. Tocopherol standards in 1% pyrogallol/ethanol are run for comparison α-tocopherol, γ-tocopherol, β-tocopherol, δ-tocopherol, and tocopherol (tocol)). Standard curves for alpha, beta, delta, and gamma tocopherol are calculated using Chemstation software (Hewlett Packard). Tocotrienol standards in 1% pyrogallol/ethanol are run for comparison (α-tocotrienol, γ-tocotrienol, β-tocotrienol, δ-tocotrienol). Standard curves for α-, β-, δ-, and γ-tocotrienol are calculated using Chemstation software (Hewlett Packard).

Carotenoid levels within transgenic corn kernels are determined by a standard protocol (Craft, *Meth. Enzymol,* 213: 185-205 (1992)). Plastiquinols and phylloquinones are determined by standard protocols (Threlfall et al., *Methods in Enzymology,* XVII, part C, 369-396 (1971); and Ramadan et al., *Eur. Food Res. Technol.,* 214(6):521-527 (2002)).

REFERENCES

Altschul, S. F. et al., J. Mol. Biol. 215:403-410, 1990.
Ausubel F M et al., Current Protocols in Molecular Biology, John Wiley & Sons, New York, N.Y., 1993.
Baldwin D et al., Cur Opin Plant Biol. 2(2):96-103, 1999.
Bateman et al., 1999, Nucleic Acids Res 27:260-262.
Baulcombe D, Arch Virol Suppl 15:189-201, 1999.
Cannon et al., Plant Molec. Biol. (1990) 15:39-47.
Ch'ng et al., Proc. Natl. Acad. Sci. USA (1989) 86:10006-10010
Christensen S et al, 9<sup>th</sup> International Conference on *Arabidopsis* Research. Univ. of Wisconsin-Madison, Jun. 24-28, 1998. Abstract 165.
Christou et al., Proc. Natl. Acad. Sci. USA (1989) 86:7500-7504.
De Block et al., Plant Physiol. (1989) 91:694-701.
Dieffenbach C and Dveksler G (Eds.) PCR Primer: A Laboratory Manual, Cold Spring Harbor Laboratory Press, MY, 1995.
Everett et al., Bio/Technology (1987) 5:1201
Feldmann et al., Science 243: 1351-1354, 1989.
Focks N and Benning C, Plant Physiol 118:91-101, 1998.
Fridborg I et al., Plant Cell 11: 1019-1032, 1999.
Harlow E and Lane D, Antibodies: A Laboratory Manual, Cold Spring Harbor Laboratory Press, 1988, New York.
Harlow E and Lane D, Using Antibodies: A Laboratory Manual, Cold Spring Harbor Laboratory Press, 1999, New York
Hayashi H et al., Science 258: 1350-1353, 1992.
Jako et al., Plant Physiology 126(2):861-74, 2001.
James D W and Dooner H K (1990) Theor Appl Genet 80, 241-245.
Jones J D et al., Transgenic Res 1:285-297 1992.
Kardailsky I et al., Science 286: 1962-1965, 1999.
Katavic V et al., Plant Physiology 108(1):399-409, 1995.
Kline et al., Nature (1987) 327:70
Kunkel T A et al., Methods Enzymol. 204:125-39, 1991.
Lemieux B., et al., 1990, Theor Appl Genet 80, 234-240.
Nakamura Y et al., 1999, Nucleic Acids Res 27:292.
Napoli, et al., Plant Cell 2:279-289, 1990.
Okuley et al., Plant Cell 6(1):147-158, 1994.
Sambrook et al., Molecular Cloning: A Laboratory Manual (Second Edition), Cold Spring Harbor Press, Plainview, N.Y., 1989.
Schaffer R, et al., Cell 93: 1219-1229, 1998.
Sheehy et al., Proc. Natl. Acad. Sci. USA (1988) 85:8805-8809.
Smith, et al, Nature 334:724-726, 1988.
Smith et al., Mol. Gen. Genetics (1990) 224:477-481.
Thompson J D et al, Nucleic Acids Res 22:4673-4680, 1994.
van der Krol et al., Biotechniques (1988) 6:958-976.
van der Krol et al., The Plant Cell (1990) 2:291-299.
Van Haaren M J J et al., Plant Mol Bio 21:625-640, 1993.
Verdaguer B et al., Plant Mol Biol 37:1055-1067, 1998.
Waterhouse, et al., Proc. Natl. Acad. Sci. USA 95:13959-13964, 1998.
Weigel D, et al., Plant Physiology, 122:1003-1013, 2000.
Wilson K et al., Plant Cell 8: 659-671, 1996.
Yadav N S et al., (1993) Plant Physiol 103, 467-476.
Krogh et al, J. Mol. Biol. 2001 305:567-580.
Day I S, et al., Genome Biol. 23; 3(10):RESEARCH0056. (2002).
Ling, V, et al., Plant Physiol 1991, 96:1196-1212.

It is claimed:

1. A method of producing a high oil phenotype in a plant, said method comprising: a) introducing into progenitor cells of the plant a plant transformation vector comprising a heterologous constitutive promoter operatively linked to a nucleotide sequence that encodes a [HIO128.5] polypeptide comprising an amino acid sequence having at least 95% sequence identity to the amino acid sequence of SEQ ID NO:2, to produce transformed cells overexpressing the polypeptide; and b) growing the transformed progenitor cells to produce a transgenic plant, wherein said polynucleotide sequence is expressed; and c) identifying said transgenic plant that exhibits a high oil phenotype relative to a plant of the same species that does not comprise the plant transformation vector.

2. The method of claim 1, wherein the nucleotide sequence encodes a [HIO128.5] polypeptide consisting of an amino acid sequence having at least 95% sequence identity to the amino acid sequence of SEQ ID NO: 2.

3. The method of claim 1, wherein the nucleotide sequence encodes a [HIO128.5] polypeptide comprising the amino acid sequence set forth as SEQ ID NO: 2.

4. The method of claim 1, wherein the nucleotide sequence encodes a [HIO128.5] polypeptide consisting of the amino acid sequence set forth as SEQ ID NO: 2.

5. A method of producing oil comprising: growing a transgenic plant comprising a plant transformation vector comprising a nucleotide sequence that encodes a [HIO128.5] polypeptide comprising an amino acid sequence having at least 95% sequence identity to the amino acid sequence of SEQ ID NO: 2, whereby the transgenic plant has a high oil phenotype relative to a plant of the same species that does not comprise the plant transformation vector; and recovering the oil from said transgenic plant.

6. The method of claim 5, wherein the nucleotide sequence encodes a [HIO128.5] polypeptide consisting of an amino acid sequence having at least 95% sequence identity to the amino acid sequence of SEQ ID NO: 2.

7. The method of claim 5, wherein the nucleotide sequence encodes a [HIO128.5] polypeptide comprising the amino acid sequence set forth as SEQ ID NO: 2.

8. The method of claim 5, wherein the nucleotide sequence encodes a [HIO128.5] polypeptide consisting of the amino acid sequence set forth as SEQ ID NO: 2.

9. The method of claim 5, wherein the oil is recovered from a seed of the plant, wherein the seed comprises the plant transformation vector.

* * * * *

UNITED STATES PATENT AND TRADEMARK OFFICE
CERTIFICATE OF CORRECTION

PATENT NO. : 7,563,942 B2  
APPLICATION NO. : 11/577713  
DATED : July 21, 2009  
INVENTOR(S) : Lightner et al.

Page 1 of 1

It is certified that error appears in the above-identified patent and that said Letters Patent is hereby corrected as shown below:

In the Specification:

Column 20, line 5, "function" should be --functions--.

Column 20, line 45, "Score= =747" should read --Score=747--.

Column 25, line 7, "subdlade withing" should read --subclade within--.

Column 25, line 40, "indicate" should read --indicates--.

Column 26, line 34 of Table 3, "CSVMV::At5g37770" should read --CsVMV::At5g37770--.

Column 28, line 45, "(OPAO for" should read --(OPA) for--.

In the Claims:

Column 41, line 31, claim 1, "a [HIO128.5] polypeptide" should read --a polypeptide--.

Column 41, line 41, claim 2, "a [HIO128.5] polypeptide" should read --a polypeptide--.

Column 41, line 45, claim 3, "a [HIO128.5] polypeptide" should read --a polypeptide--.

Column 41, line 48, claim 4, "a [HIO128.5] polypeptide" should read --a polypeptide--.

Column 42, line 28, claim 5, "a [HIO128.5] polypeptide" should read --a polypeptide--.

Column 42, line 36, claim 6, "a [HIO128.5] polypeptide" should read --a polypeptide--.

Column 42, line 40, claim 7, "a [HIO128.5] polypeptide" should read --a polypeptide--.

Column 42, line 43, claim 8, "a [HIO128.5] polypeptide" should read --a polypeptide--.

Signed and Sealed this  
First Day of April, 2014

Michelle K. Lee  
*Deputy Director of the United States Patent and Trademark Office*